US 12,144,754 B2

(12) United States Patent
Marmur et al.

(10) Patent No.: US 12,144,754 B2
(45) Date of Patent: *Nov. 19, 2024

(54) SELF-ORIENTING ENDOVASCULAR DELIVERY SYSTEM

(71) Applicant: ENDOSPAN LTD., Herzilyia Pituach (IL)

(72) Inventors: Yaniv Marmur, Yokneam Moshava (IL); Or Zigelboim, Ness Ziona (IL); Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,754

(22) Filed: Oct. 23, 2023

(65) Prior Publication Data

US 2024/0050253 A1    Feb. 15, 2024

Related U.S. Application Data

(60) Continuation of application No. 17/840,786, filed on Jun. 15, 2022, now Pat. No. 11,813,185, which is a
(Continued)

(51) Int. Cl.
*A61F 2/07*         (2013.01)
*A61F 2/856*        (2013.01)
*A61F 2/966*        (2013.01)

(52) U.S. Cl.
CPC .............. *A61F 2/9662* (2020.05); *A61F 2/07* (2013.01); *A61F 2/856* (2013.01); *A61F 2230/008* (2013.01)

(58) Field of Classification Search
CPC .......... A61F 2/07; A61F 2/856; A61F 2/9662; A61F 2/95; A61F 2/9522; A61F 2/954;
(Continued)

(56) References Cited

U.S. PATENT DOCUMENTS 6,132,417 A    10/2000  Kiesz
6,332,893 B1   12/2001  Mortier et al.
(Continued)

FOREIGN PATENT DOCUMENTS

WO        98/06355 A1    2/1998
WO       2002/028321     4/2002
(Continued)

OTHER PUBLICATIONS

An International Search Report and a Written Opinion both dated Apr. 22, 2016, which issued during the prosecution of Applicant's PCT/IL2016/050049.
(Continued)

*Primary Examiner* — Majid Jamialahmadi
(74) *Attorney, Agent, or Firm* — Sughrue Mion, PLLC

(57) ABSTRACT

An elongate delivery shaft assembly (30) includes an outer covering shaft (38) and an inner support shaft (40). When the delivery shaft assembly (30) is unconstrained and a stent-graft (20) is removably constrained in a radially-compressed delivery state along a distal end portion (34) of the delivery shaft assembly (30), radially between the outer covering shaft (38) and the inner support shaft (40): (a) the delivery shaft assembly (30) is shaped so as to define a self-orienting portion (50), which (i) is shaped so as to define at least proximal and distal curved portions (52A, 52B), the proximal curved portion (52A) disposed more proximal than the distal curved portion (52B), and (ii) at least one point of inflection (53) on a central longitudinal axis (36) of the delivery shaft assembly (30) longitudinally between the proximal and the distal curved portions (52A, 52B), and (b) respective smallest radii of curvature of the proximal and the distal curved portions (52A, 52B), measured at the central longitudinal axis (36), are each between 2.5 and 12 cm.

23 Claims, 11 Drawing Sheets

Related U.S. Application Data continuation of application No. 16/909,259, filed on Jun. 23, 2020, now Pat. No. 11,389,313, which is a division of application No. 15/548,180, filed as application No. PCT/IL2016/050049 on Jan. 14, 2016, now abandoned.

(60) Provisional application No. 62/110,659, filed on Feb. 2, 2015.

(58) Field of Classification Search
CPC ........ A61F 2/958; A61F 2/9661; A61F 2/966; A61F 2002/9665; A61F 2002/072; A61F 2002/075; A61F 2002/077
See application file for complete search history.

(56) References Cited

U.S. PATENT DOCUMENTS

| | | | |
|---|---|---|---|
| 8,333,800 | B2 | 12/2012 | Bruszewski et al. |
| 8,506,622 | B2 | 8/2013 | Bruszewski et al. |
| 9,980,838 | B2 | 5/2018 | Syed |
| 2002/0013617 | A1 | 1/2002 | Matsutani et al. |
| 2003/0088305 | A1 | 5/2003 | Van Schie et al. |
| 2004/0186566 | A1 | 9/2004 | Hindrichs et al. |
| 2006/0190070 | A1 | 8/2006 | Dieck et al. |
| 2009/0254170 | A1 | 10/2009 | Hartley et al. |
| 2010/0268327 | A1 | 10/2010 | Bruszewski et al. |
| 2011/0208289 | A1 | 8/2011 | Shalev |
| 2012/0123464 | A1 | 5/2012 | Rasmussen et al. |
| 2013/0013050 | A1 | 1/2013 | Shalev et al. |
| 2013/0079870 | A1* | 3/2013 | Roeder ............... A61F 2/07 623/1.35 |
| 2013/0197454 | A1 | 8/2013 | Shibata et al. |
| 2013/0204311 | A1 | 8/2013 | Kunis |
| 2013/0338753 | A1 | 12/2013 | Geusen |
| 2014/0316510 | A1 | 10/2014 | Berra |

FOREIGN PATENT DOCUMENTS

| | | |
|---|---|---|
| WO | 2004/045463 | 6/2004 |
| WO | 2006/028925 A1 | 3/2006 |
| WO | 2008098255 A2 | 8/2008 |
| WO | 2012/039748 | 3/2012 |
| WO | 2014/141232 | 9/2014 |
| WO | 2014/188412 | 11/2014 |
| WO | 2016/113731 | 7/2016 |

OTHER PUBLICATIONS

Final Office Action dated Mar. 27, 2020 issued in U.S. Appl. No. 15/548,180.

Interview Summary dated Dec. 16, 2019 issued in U.S. Appl. No. 15/548,180.

Non-Final Office dated Jul. 30, 2019 issued in U.S. Appl. No. 15/548,180.

Notice of Allowance dated May 13, 2022 in U.S. Appl. No. 16/909,259.

Shammari Ma et al., "Use of through-and-through guidewire for delivering large stent-grafts into the distal aortic arch," Cardiovasc Intervent Radiol 23, 237-238 (May 2000).

U.S. Appl. No. 62/110,659, filed Feb. 2, 2015.

Notice of Allowance dated Jul. 12, 2023 in U.S. Appl. No. 17/840,786.

* cited by examiner

SELF-ORIENTING ENDOVASCULAR DELIVERY SYSTEM

CROSS-REFERENCE TO RELATED APPLICATIONS

The present application is a continuation of U.S. application Ser. No. 17/840,786, filed Jun. 15, 2022, now U.S. Pat. No. 11,813,185, which is a continuation of U.S. application Ser. No. 16/909,259, filed Jun. 23, 2020, now U.S. Pat. No. 11,389,313, which is a divisional of U.S. application Ser. No. 15/548,180, filed Aug. 2, 2017, now abandoned, which is the U.S. national stage of International Application PCT/IL2016/050049, filed Jan. 14, 2016, which published as PCT Publication WO 2016/125137 and claims priority from U.S. Provisional Application No. 62/110,659, filed Feb. 2, 2015, all of which applications are assigned to the assignee of the present application and are incorporated herein by reference.

FIELD OF THE APPLICATION

The present invention relates generally to implantable medical devices, and specifically to delivery systems for implantable stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 24 Fr or lower (3 Fr=1 millimeter), a true percutaneous approach may be used, because vascular closure devices are available for proper closure of such puncture sites.

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification. Type A dissections involve the ascending aorta and/or aortic arch, and possibly the descending aorta. Type B dissections involve the descending aorta or the arch (distal to right brachiocephalic artery origin), without involvement of the ascending aorta.

SUMMARY OF THE APPLICATION

In applications of the present invention, an endovascular system is provided that comprises a stent-graft and an elongate delivery shaft assembly, which comprises an outer covering shaft and an inner support shaft. The stent-graft may be used to treat a blood vessel, such as an aortic arch, suffering from an aneurysm or a dissection, or, more generally, that is pathologically dilated. When the delivery shaft assembly is unconstrained and the stent-graft is removably constrained in a radially-compressed delivery state along a distal end portion of the delivery shaft assembly, radially between the outer covering shaft and the inner support shaft, the delivery shaft assembly (typically the distal end portion thereof) is shaped so as to define a self-orienting portion, which is shaped so as to define at least proximal and distal curved portions, and at least one point of inflection on a central longitudinal axis of the delivery shaft assembly, between the proximal and the distal portions. The curved portions may, for example, together be sinusoidal. Typically, respective smallest radii of curvature of the proximal and the distal curved portions, measured at the central longitudinal axis, are each between 2.5 and 12 cm.

The curved portions cause the self-orienting portion to automatically rotationally orient itself to a desired rotation in the blood vessel. Therefore, manual rotation of the delivery shaft assembly is generally not necessary. The proximal end portion is typically quite long, and thus transmits proximal torque poorly to the distal end portion. As a result, manual rotation of the delivery shaft assembly is often difficult or impossible, and/or may result in damage to the delivery shaft assembly, or in an unexpected rotation of the stent-graft, because of the rotational static torque accumulated in the delivery system during rotation thereof at a user handle. In addition, it is generally difficult, if not impossible, to properly rotationally orient the delivery shaft assembly before and/or during introduction into the vasculature, because the tortuous vasculature changes the rotation of the delivery shaft assembly as it is advanced.

For some applications, when in the radially-expanded state, the stent-graft may be shaped so as to define a superior lateral opening and an inferior lateral opening. Typically, at least when the stent-graft is unconstrained in the radially-expanded state, the superior lateral opening faces in a first radial direction, and the inferior lateral opening faces in a second radially direction generally circumferentially opposite the first radial direction. Typically, the stent-graft is rotationally disposed in the delivery shaft assembly such that, upon deployment therefrom, the superior lateral opening is rotationally aligned with the left common carotid artery.

For some applications, the self-orienting portion defines a best-fit straight axis line having a minimum sum of squares of distances between the best-fit straight axis line and the central longitudinal axis along the proximal and the distal curved portions. The proximal and the distal curved portions have respective proximal and distal peaks with respect to the best-fit straight axis line. The proximal and the distal peaks define respective proximal and distal vectors, which (a) have respective origins on the best-fit straight axis line, (b) are perpendicular to the best-fit straight axis line, and (c) intersect the proximal and the distal peaks, respectively. An angle between the proximal and the distal vectors is at least 120 degrees.

Alternatively or additionally, for some applications, the delivery shaft assembly is shaped so as to define a proximal straight portion which has a length of at least 50 cm, and is disposed more proximal than the self-orienting portion. The central longitudinal axis along the proximal straight portion defines a straight axis line. The proximal and the distal curved portions have respective proximal and distal peaks with respect to the straight axis line, which define proximal and distal vectors that (a) have respective origins on the straight axis line, (b) are perpendicular to the straight axis line, and (c) intersect the proximal and the distal peaks, respectively. Typically, an angle between the proximal and the distal vectors is at least 120 degrees. For some applications, respective distances between (a) the straight axis line and (b) the proximal and the distal peaks are each between 3 and 10 cm.

There is therefore provided, in accordance with an application of the present invention, apparatus including an endovascular system, which includes:
- a stent-graft, which is configured to transition from a radially-compressed delivery state to a radially-expanded state; and
- an elongate delivery shaft assembly, which has proximal and distal end portions, defines a central longitudinal axis, and includes an outer covering shaft and an inner support shaft,
- wherein when the delivery shaft assembly is unconstrained and the stent-graft is removably constrained in the radially-compressed delivery state along the distal end portion of the delivery shaft assembly, radially between the outer covering shaft and the inner support shaft:
  - the delivery shaft assembly is shaped so as to define a self-orienting portion, which (a) is shaped so as to define at least proximal and distal curved portions, wherein the proximal curved portion is disposed more proximal than the distal curved portion, and (b) at least one point of inflection on the central longitudinal axis longitudinally between the proximal and the distal curved portions, and
  - respective smallest radii of curvature of the proximal and the distal curved portions, measured at the central longitudinal axis, are each between 2.5 and 12 cm.

For some applications, the distal end portion of the delivery shaft assembly is shaped so as to define the self-orienting portion.

For some applications, at least 70% of a total length of the stent-graft, measured along the central longitudinal axis, axially overlaps the self-orienting portion of the delivery shaft assembly, when the stent-graft is removably constrained in the radially-compressed delivery state along the distal end portion of the delivery shaft assembly, radially between the outer covering shaft and the inner support shaft.

For some applications, the proximal and the distal curved portions together define a sinusoid. For some applications, the proximal and the distal curved portions have a same curve shape. For some applications, the proximal and the distal curved portions are the same size.

For some applications:
- the stent-graft is shaped so as to define a superior lateral opening,
- when the delivery shaft assembly is unconstrained and the stent-graft is removably constrained in the radially-compressed delivery state along the distal end portion of the delivery shaft assembly, radially between outer the covering shaft and the inner support shaft, the stent-graft is axially disposed in the delivery shaft assembly such that the superior lateral opening is in the self-orienting portion, and
- when the delivery shaft assembly is unconstrained and the stent-graft is removably constrained in the radially-compressed delivery state along the distal end portion of the delivery shaft assembly, radially between outer the covering shaft and the inner support shaft, the stent-graft is rotationally oriented with respect to the delivery shaft assembly so as to, upon release of the stent-graft from the delivery shaft assembly without rotation of the stent-graft, define a line between (a) the central longitudinal axis and (b) a central axis of the superior lateral opening parallel to the central longitudinal axis, which line is perpendicular to the central longitudinal axis, and forms an angle of no more than 30 degrees (e.g., no more than 15 degrees) with a proximal best-fit plane defined by the proximal curved portion, wherein the proximal best-fit plane is defined when the delivery shaft assembly is unconstrained and the stent-graft is removably constrained in the radially-compressed delivery state along the distal end portion of the delivery shaft assembly, radially between the outer covering shaft and the inner support shaft. For some applications, the stent-graft is shaped so as to further define an inferior lateral opening, and the superior and the inferior lateral openings face in respective radial directions that are generally opposite one another when the stent-graft is in the radially-expanded state.

For some applications, the delivery shaft assembly is shaped so as not to define an additional curved portion, in addition to the proximal and the distal curved portions, having a smallest radius of curvature, measured at the central longitudinal axis, of between 2.5 and 12 cm.

For some applications, the delivery shaft assembly is further shaped so as to define a distal straight portion which (a) is disposed distal to the self-orienting portion, and (b) has a length of at least 10 mm, when the delivery shaft assembly is unconstrained and the stent-graft is removably constrained in the radially-compressed delivery state along the distal end portion of the delivery shaft assembly, radially between the outer covering shaft and the inner support shaft.

For some applications, the delivery shaft assembly is further shaped so as to define a distal straight portion which (a) is disposed distal to the self-orienting portion, and (b) has a length equal to at least 10% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, the endovascular system further includes a user handle, which is fixed to the outer covering shaft and the inner support shaft at the proximal shaft end of the delivery shaft assembly, and is configured to effect longitudinal displacement between the outer covering shaft and the inner support shaft, thereby releasing the stent-graft from the delivery shaft assembly, and allowing the stent-graft to transition from the radially-compressed delivery state to the radially-expanded state.

For some applications, the apparatus is for use with a guidewire, and the inner support shaft is shaped so as to define at least one internal bore, which is sized for passage therethrough of the guidewire.

For some applications, the respective smallest radii of curvature of the proximal and the distal curved portions are each between 4 and 10 cm.

For some applications, the outer covering shaft includes polyether block amide (PEBA). For some applications, the inner support shaft includes polyether ether ketone (PEEK).

For some applications, the endovascular system further includes a distal tip, which is fixed to and extends distally beyond a distal end of the inner support shaft. For some applications, the distal tip is conical.

For some applications, when the delivery shaft assembly is unconstrained and the stent-graft is removably constrained in the radially-compressed delivery state along the distal end portion of the delivery shaft assembly, radially between the outer covering shaft and the inner support shaft:
  the self-orienting portion defines a best-fit straight axis line having a minimum sum of squares of distances between the best-fit straight axis line and the central longitudinal axis along the proximal and the distal curved portions,
  the proximal and the distal curved portions have respective proximal and distal peaks with respect to the best-fit straight axis line, which define respective proximal and distal vectors, which (i) have respective origins on the best-fit straight axis line, (ii) are perpendicular to the best-fit straight axis line, and (iii) intersect the proximal and the distal peaks, respectively, and
  an angle between the proximal and the distal vectors is at least 120 degrees, e.g., at least 150 degrees.

For some applications, when the delivery shaft assembly is unconstrained and the stent-graft is removably constrained in the radially-compressed delivery state along the distal end portion of the delivery shaft assembly, radially between the outer covering shaft and the inner support shaft:
  the self-orienting portion defines a best-fit straight axis line having a minimum sum of squares of distances between the best-fit straight axis line and the central longitudinal axis along the proximal and the distal curved portions,
  the proximal and the distal curved portions have respective proximal and distal peaks with respect to the best-fit straight axis line, and
  respective distances between (a) the best-fit straight axis line and (b) the proximal and the distal peaks are each at least 3 cm, e.g., between 3 and 10 cm.

For some applications, when the delivery shaft assembly is unconstrained and the stent-graft is removably constrained in the radially-compressed delivery state along the distal end portion of the delivery shaft assembly, radially between the outer covering shaft and the inner support shaft:
  the self-orienting portion defines a best-fit straight axis line having a minimum sum of squares of distances between the best-fit straight axis line and the central longitudinal axis along the proximal and the distal curved portions, and
  the delivery shaft assembly is shaped so as not to define an additional curved portion, in addition to the proximal and the distal curved portions, having a distance between the best-fit straight axis line and a peak of the additional curved portion, with respect to the best-fit straight axis line, of at least 3 cm.

For some applications:
  the self-orienting portion defines a best-fit straight axis line having a minimum sum of squares of distances between the best-fit straight axis line and the central longitudinal axis along the proximal and the distal curved portions, and
  respective axial lengths of the proximal and the distal curved portions, measured parallel to the best-fit straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications:
  the self-orienting portion defines a best-fit straight axis line having a minimum sum of squares of distances between the best-fit straight axis line and the central longitudinal axis along the proximal and the distal curved portions, and
  respective axial lengths of the proximal and the distal curved portions, measured parallel to the best-fit straight axis line, are each between 25% and 125% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, when the delivery shaft assembly is unconstrained and the stent-graft is removably constrained in the radially-compressed delivery state along the distal end portion of the delivery shaft assembly, radially between the outer covering shaft and the inner support shaft:
  the self-orienting portion defines a best-fit straight axis line having a minimum sum of squares of distances between the best-fit straight axis line and the central longitudinal axis along the proximal and the distal curved portions,
  the proximal and the distal curved portions have respective proximal and distal peaks with respect to the best-fit straight axis line, and
  a distance between the proximal and the distal peaks, measured parallel to the best-fit straight axis line, is between 5 and 20 cm.

For some applications, when the delivery shaft assembly is unconstrained and the stent-graft is removably constrained in the radially-compressed delivery state along the distal end portion of the delivery shaft assembly, radially between the outer covering shaft and the inner support shaft:
  the self-orienting portion defines a best-fit straight axis line having a minimum sum of squares of distances between the best-fit straight axis line and the central longitudinal axis along the proximal and the distal curved portions,
  the proximal and the distal curved portions have respective proximal and distal peaks with respect to the best-fit straight axis line, and
  a distance between the proximal and the distal peaks, measured parallel to the best-fit straight axis line, is between 50% and 120% of a length of the stent-graft, measured along the central longitudinal axis.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions have respective proximal and distal peaks with respect to the best-fit straight axis line, and a distance between the distal peak and a distal end of the outer covering shaft, measured parallel to the best-fit straight axis line, is between 3 and 8 cm.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions have respective proximal and distal peaks with respect to the best-fit straight axis line, and a distance between distal peak and a distal end of the outer covering shaft, measured parallel to the best-fit straight axis line, is between 15% and 40% of a length of the stent-graft, measured along the central longitudinal axis.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions have respective proximal and distal peaks with respect to the best-fit straight axis line, and a distance between the proximal peak and a proximal end of the outer covering shaft, measured parallel to the best-fit straight axis line, is between 50 and 120 cm.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions define respective proximal and distal best-fit planes, an angle between the proximal and the distal planes is no more than 60 degrees, and the proximal and the distal best-fit planes intersect at an intersection line that is not parallel to the best-fit straight axis line.

For some applications, the angle between the proximal and the distal planes is no more than 40 degrees. For some applications, the angle between the proximal and the distal planes is at least 30 degrees.

For some applications, (a) a third vector parallel to the intersection line and (b) a fourth vector parallel to the best-fit straight axis line form an angle of between 30 and 90 degrees, e.g., between 60 and 90 degrees.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the delivery shaft assembly is shaped so as to define a proximal straight portion which is disposed more proximal than the self-orienting portion, and has a length of at least 50 cm, the central longitudinal axis along the proximal straight portion defines a straight axis line, and the proximal and the distal curved portions have respective proximal and distal peaks with respect to the straight axis line.

For some applications, the proximal and distal peaks define proximal and distal vectors, respectively, which (i) have respective origins on the straight axis line, (ii) are perpendicular to the straight axis line, and (iii) intersect the proximal and the distal peaks, respectively, and an angle between the proximal and the distal vectors is at least 120 degrees (e.g., at least 150 degrees), when the delivery shaft assembly is unconstrained and the stent-graft is removably constrained in the radially-compressed delivery state along the distal end portion of the delivery shaft assembly, radially between the outer covering shaft and the inner support shaft.

For some applications, respective distances between (a) the straight axis line and (b) the proximal and the distal peaks are each at least 3 cm, when the delivery shaft assembly is unconstrained and the stent-graft is removably constrained in the radially-compressed delivery state along the distal end portion of the delivery shaft assembly, radially between the outer covering shaft and the inner support shaft. For some applications, the respective distances are each between 3 and 10 cm.

For some applications, the delivery shaft assembly is shaped so as not to define an additional curved portion, in addition to the proximal and the distal curved portions, having a distance between the straight axis line and a peak of the additional curved portion of at least 3 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, respective axial lengths of the proximal and the distal curved portions, measured parallel to the straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, respective axial lengths of the proximal and the distal curved portions, measured parallel to the straight axis line, are each between 25% and 125% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, a distance between the proximal and the distal peaks, measured parallel to the straight axis line, is between 5 and 20 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, a distance between the proximal and the distal peaks, measured parallel to the straight axis line, is between 50% and 120% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, a distance between the distal peak and a distal end of the outer covering shaft, measured parallel to the straight axis line, is between 3 and 8 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, a distance between distal peak and a distal end of the outer covering shaft, measured parallel to the straight axis line, is between 15% and 40% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, a distance between the proximal peak and a proximal end of the outer covering shaft, measured parallel to the straight axis line, is between 50 and 120 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, when the delivery shaft assembly is unconstrained and the stent-graft is removably constrained in the radially-compressed delivery state along the distal end portion of the delivery shaft assembly, radially between the outer covering shaft and the inner support shaft:

the proximal and the distal curved portions define respective proximal and distal best-fit planes, an angle between the proximal and the distal planes is no more than 60 degrees, and the proximal and the distal best-fit planes intersect at an intersection line that is not parallel to the straight axis line.

For some applications, the angle between the proximal and the distal planes is no more than 40 degrees. For some applications, the angle between the proximal and the distal planes is at least 30 degrees.

For some applications, (a) a third vector parallel to the intersection line and (b) a fourth vector parallel to the straight axis line form an angle of between 30 and 90 degrees, e.g., between 60 and 90 degrees.

There is further provided, in accordance with an application of the present invention, a method for treating a subject, including:

providing an endovascular system that includes (a) a stent-graft, which is configured to transition from a radially-compressed delivery state to a radially-expanded state, and (b) an elongate delivery shaft assembly, which has proximal and distal end portions, defines a central longitudinal axis, and includes an outer covering shaft and an inner support shaft, wherein when the delivery shaft assembly is unconstrained and the stent-graft is removably constrained in the radially-compressed delivery state along the distal end portion of the delivery shaft assembly, radially between the outer covering shaft and the inner support shaft, (a) the delivery shaft assembly is shaped so as to define a self-orienting portion, which (i) is shaped so as to define at least proximal and distal curved portions, wherein the proximal curved portion is disposed more proximal than the distal curved portion, and (ii) at least one point of inflection on the central longitudinal axis longitudinally between the proximal and the distal curved portions, and (b) respective smallest radii of curvature of the proximal and the distal curved portions, measured at the central longitudinal axis, are each between 2.5 and 12 cm;

while the stent-graft is removably constrained in the radially-compressed delivery state along the distal end portion of the delivery shaft assembly, transvascularly introducing the delivery shaft assembly into a blood vessel of the subject and advancing the distal end portion of the delivery shaft assembly to a target site in the blood vessel, such that the self-orienting portion assumes a desired rotational orientation at the target site; and releasing the stent-graft from the distal end portion of the delivery shaft assembly by proximally withdrawing the outer covering shaft while holding the inner support shaft in place.

For some applications, transvascularly introducing the elongate delivery shaft assembly into the blood vessel and advancing the distal end portion of the delivery shaft assembly to the target site includes transvascularly introducing the elongate delivery shaft assembly into a descending aorta and advancing the distal end portion of the delivery shaft assembly to an aortic arch.

For some applications, providing the endovascular system includes providing the endovascular system in which the distal end portion of the delivery shaft assembly is shaped so as to define the self-orienting portion.

For some applications, providing the endovascular system includes providing the endovascular system in which at least 70% of a total length of the stent-graft, measured along the central longitudinal axis, axially overlaps the self-orienting portion of the delivery shaft assembly, when the stent-graft is removably constrained in the radially-compressed delivery state along the distal end portion of the delivery shaft assembly, radially between the outer covering shaft and the inner support shaft.

For some applications, providing the endovascular system includes providing the endovascular system in which the proximal and the distal curved portions together define a sinusoid. For some applications, providing the endovascular system includes providing the endovascular system in which the proximal and the distal curved portions have a same curve shape. For some applications, providing the endovascular system includes providing the endovascular system in which the proximal and the distal curved portions are the same size.

For some applications, providing the endovascular system includes providing the endovascular system in which:
- the stent-graft is shaped so as to define a superior lateral opening,
- when the delivery shaft assembly is unconstrained and the stent-graft is removably constrained in the radially-compressed delivery state along the distal end portion of the delivery shaft assembly, radially between outer the covering shaft and the inner support shaft, the stent-graft is axially disposed in the delivery shaft assembly such that the superior lateral opening is in the self-orienting portion, and
- when the delivery shaft assembly is unconstrained and the stent-graft is removably constrained in the radially-compressed delivery state along the distal end portion of the delivery shaft assembly, radially between outer the covering shaft and the inner support shaft, the stent-graft is rotationally oriented with respect to the delivery shaft assembly so as to, upon release of the stent-graft from the delivery shaft assembly without rotation of the stent-graft, define a line between (a) the central longitudinal axis and (b) a central axis of the superior lateral opening parallel to the central longitudinal axis, which line is perpendicular to the central longitudinal axis, and forms an angle of no more than 30 degrees (e.g., no more than 15 degrees) with a proximal best-fit plane defined by the proximal curved portion, wherein the proximal best-fit plane is defined when the delivery shaft assembly is unconstrained and the stent-graft is removably constrained in the radially-compressed delivery state along the distal end portion of the delivery shaft assembly, radially between the outer covering shaft and the inner support shaft.

For some applications, the stent-graft is shaped so as to further define an inferior lateral opening, and the superior and the inferior lateral openings face in respective radial directions that are generally opposite one another when the stent-graft is in the radially-expanded state.

For some applications, providing the endovascular system includes providing the endovascular system in which the delivery shaft assembly is shaped so as not to define an additional curved portion, in addition to the proximal and the distal curved portions, having a smallest radius of curvature, measured at the central longitudinal axis, of between 2.5 and 12 cm.

For some applications, providing the endovascular system includes providing the endovascular system in which the delivery shaft assembly is further shaped so as to define a distal straight portion which (a) is disposed distal to the self-orienting portion, and (b) has a length of at least 10 mm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which the delivery shaft assembly is further shaped so as to define a distal straight portion which (a) is disposed distal to the self-orienting portion, and (b) has a length equal to at least 10% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications:
- providing the endovascular system includes providing the endovascular system in which the endovascular system further includes a user handle, which is fixed to the outer covering shaft and the inner support shaft at the proximal shaft end of the delivery shaft assembly, and
- proximally withdrawing the outer covering shaft while holding the inner support shaft in place includes actuating the user handle to effect longitudinal displacement between the outer covering shaft and the inner support shaft.

For some applications:
- providing the endovascular system includes providing the endovascular system in which the inner support shaft is shaped so as to define at least one internal bore, which is sized for passage therethrough of a guidewire, and
- transvascularly introducing the delivery shaft assembly into the blood vessel of the subject and advancing the distal end portion of the delivery shaft assembly to the target site includes:
  - transvascularly introducing the guidewire into the blood vessel; and
  - advancing the distal end portion of the delivery shaft assembly over the guidewire while a portion of the guidewire is in the internal bore.

For some applications, providing the endovascular system includes providing the endovascular system in which the respective smallest radii of curvature of the proximal and the distal curved portions are each between 4 and 10 cm.

For some applications, providing the endovascular system includes providing the endovascular system in which the outer covering shaft includes polyether block amide (PEBA). For some applications, providing the endovascular system includes providing the endovascular system in which the inner support shaft includes polyether ether ketone (PEEK).

For some applications, providing the endovascular system includes providing the endovascular system in which the endovascular system further includes a distal tip, which is fixed to and extends distally beyond a distal end of the inner support shaft. For some applications, providing the endovascular system includes providing the endovascular system in which the distal tip is conical.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, which define respective proximal and distal vectors, which (i) have respective origins on the best-fit straight axis line, (ii) are perpendicular to the best-fit straight axis line, and (iii) intersect the proximal and the distal peaks, respectively, and
- an angle between the proximal and the distal vectors is at least 120 degrees.

For some applications, providing the endovascular system includes providing the endovascular system in which the angle between the proximal and the distal vectors is at least 150 degrees.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- respective distances between (a) the best-fit straight axis line and (b) the proximal and the distal peaks are each at least 3 cm.

For some applications, providing the endovascular system includes providing the endovascular system in which the respective distances are each between 3 and 10 cm.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions, and
- the delivery shaft assembly is shaped so as not to define an additional curved portion, in addition to the proximal and the distal curved portions, having a distance between the best-fit straight axis line and a peak of the additional curved portion, with respect to the best-fit straight axis line, of at least 3 cm.

For some applications, providing the endovascular system includes providing the endovascular system in which:
- the self-orienting portion defines a best-fit straight axis line having a minimum sum of squares of distances between the best-fit straight axis line and the central longitudinal axis along the proximal and the distal curved portions, and
- respective axial lengths of the proximal and the distal curved portions, measured parallel to the best-fit straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which:
- the self-orienting portion defines a best-fit straight axis line having a minimum sum of squares of distances between the best-fit straight axis line and the central longitudinal axis along the proximal and the distal curved portions, and
- respective axial lengths of the proximal and the distal curved portions, measured parallel to the best-fit straight axis line, are each between 25% and 125% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- a distance between the proximal and the distal peaks, measured parallel to the best-fit straight axis line, is between 5 and 20 cm.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- a distance between the proximal and the distal peaks, measured parallel to the best-fit straight axis line, is between 50% and 120% of a length of the stent-graft, measured along the central longitudinal axis.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- a distance between the distal peak and a distal end of the outer covering shaft, measured parallel to the best-fit straight axis line, is between 3 and 8 cm.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions have respective proximal and distal peaks with respect to the best-fit straight axis line, and a distance between distal peak and a distal end of the outer covering shaft, measured parallel to the best-fit straight axis line, is between 15% and 40% of a length of the stent-graft, measured along the central longitudinal axis.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions have respective proximal and distal peaks with respect to the best-fit straight axis line, and a distance between the proximal peak and a proximal end of the outer covering shaft, measured parallel to the best-fit straight axis line, is between 50 and 120 cm.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:

the self-orienting portion defines a best-fit straight axis line having a minimum sum of squares of distances between the best-fit straight axis line and the central longitudinal axis along the proximal and the distal curved portions, the proximal and the distal curved portions define respective proximal and distal best-fit planes, an angle between the proximal and the distal planes is no more than 60 degrees, and the proximal and the distal best-fit planes intersect at an intersection line that is not parallel to the best-fit straight axis line.

For some applications, providing the endovascular system includes providing the endovascular system in which the angle between the proximal and the distal planes is no more than 40 degrees. For some applications, providing the endovascular system includes providing the endovascular system in which the angle between the proximal and the distal planes is at least 30 degrees.

For some applications, providing the endovascular system includes providing the endovascular system in which (a) a third vector parallel to the intersection line and (b) a fourth vector parallel to the best-fit straight axis line form an angle of between 30 and 90 degrees, e.g., between 60 and 90 degrees.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:

the delivery shaft assembly is shaped so as to define a proximal straight portion which is disposed more proximal than the self-orienting portion, and has a length of at least 50 cm, the central longitudinal axis along the proximal straight portion defines a straight axis line, and the proximal and the distal curved portions have respective proximal and distal peaks with respect to the straight axis line.

For some applications, providing the endovascular system includes providing the endovascular system in which the proximal and distal peaks define proximal and distal vectors, respectively, which (i) have respective origins on the straight axis line, (ii) are perpendicular to the straight axis line, and (iii) intersect the proximal and the distal peaks, respectively, wherein an angle between the proximal and the distal vectors is at least 120 degrees (e.g., at least 150 degrees), when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which respective distances between (a) the straight axis line and (b) the proximal and the distal peaks are each at least 3 cm, when the delivery shaft assembly is unconstrained and the stent-graft is removably constrained in the radially-compressed delivery state along the distal end portion of the delivery shaft assembly, radially between the outer covering shaft and the inner support shaft. For some applications, providing the endovascular system includes providing the endovascular system in which the respective distances are each between 3 and 10 cm.

For some applications, providing the endovascular system includes providing the endovascular system in which the delivery shaft assembly is shaped so as not to define an additional curved portion, in addition to the proximal and the distal curved portions, having a distance between the straight axis line and a peak of the additional curved portion of at least 3 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which respective axial lengths of the proximal and the distal curved portions, measured parallel to the straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which respective axial lengths of the proximal and the distal curved portions, measured parallel to the straight axis line, are each between 25% and 125% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which a distance between the proximal and the distal peaks, measured parallel to the straight axis line, is between 5 and 20 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which a distance between the proximal and the distal peaks, measured parallel to the straight axis line, is between 50% and 120% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which a distance between the distal peak and a distal end of the outer covering shaft, measured parallel to the straight axis line, is between 3 and 8 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which a distance between distal peak and a distal end of the outer covering shaft, measured parallel to the straight axis line, is between 15% and 40% of a length of the stent-graft, measured along the central longitudinal axis, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which a distance between the proximal peak and a proximal end of the outer covering shaft, measured parallel to the straight axis line, is between 50 and 120 cm, when the delivery shaft assembly is unconstrained and the stent-graft is removably constrained in the radially-compressed delivery state along the distal end portion of the delivery shaft assembly, radially between the outer covering shaft and the inner support shaft.

For some applications, providing the endovascular system includes providing the endovascular system in which, when the delivery shaft assembly is unconstrained and the stent-graft is removably constrained in the radially-compressed delivery state along the distal end portion of the delivery shaft assembly, radially between the outer covering shaft and the inner support shaft:
  the proximal and the distal curved portions define respective proximal and distal best-fit planes,
  an angle between the proximal and the distal planes is no more than 60 degrees, and
  the proximal and the distal best-fit planes intersect at an intersection line that is not parallel to the straight axis line.

For some applications, providing the endovascular system includes providing the endovascular system in which the angle between the proximal and the distal planes is no more than 40 degrees. For some applications, providing the endovascular system includes providing the endovascular system in which the angle between the proximal and the distal planes is at least 30 degrees.

For some applications, providing the endovascular system includes providing the endovascular system in which (a) a third vector parallel to the intersection line and (b) a fourth vector parallel to the straight axis line form an angle of between 30 and 90 degrees, e.g., between 60 and 90 degrees.

The present invention will be more fully understood from the following detailed description of embodiments thereof, taken together with the drawings, in which:

DETAILED DESCRIPTION OF APPLICATIONS

Figure 1A:
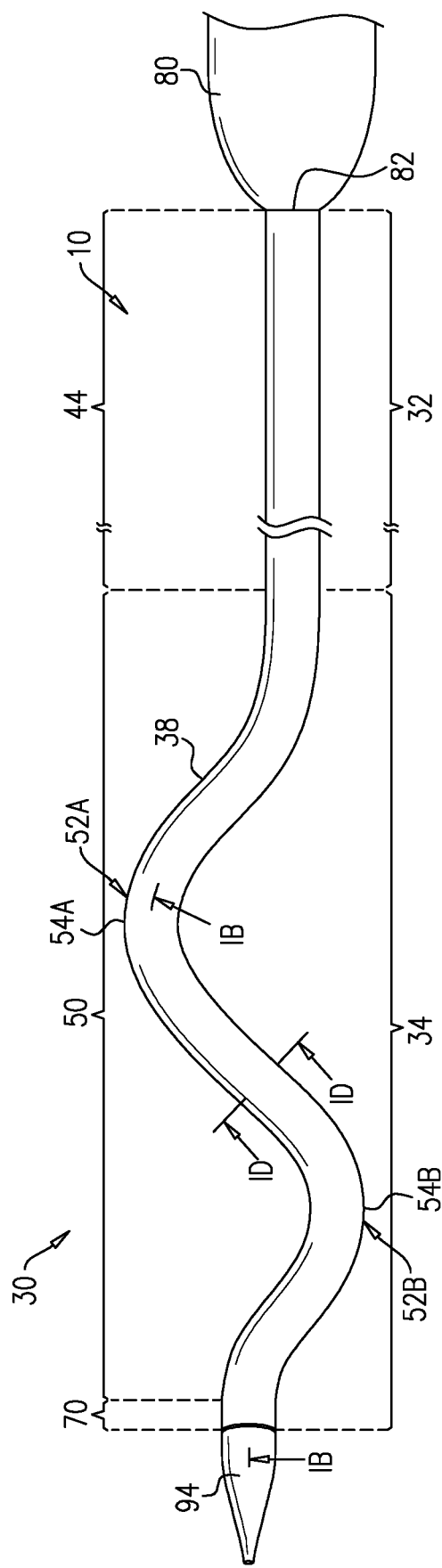
FIGS. 1A-D are schematic illustrations of an endovascular system, in accordance with an application of the present invention.
Figure 1B:
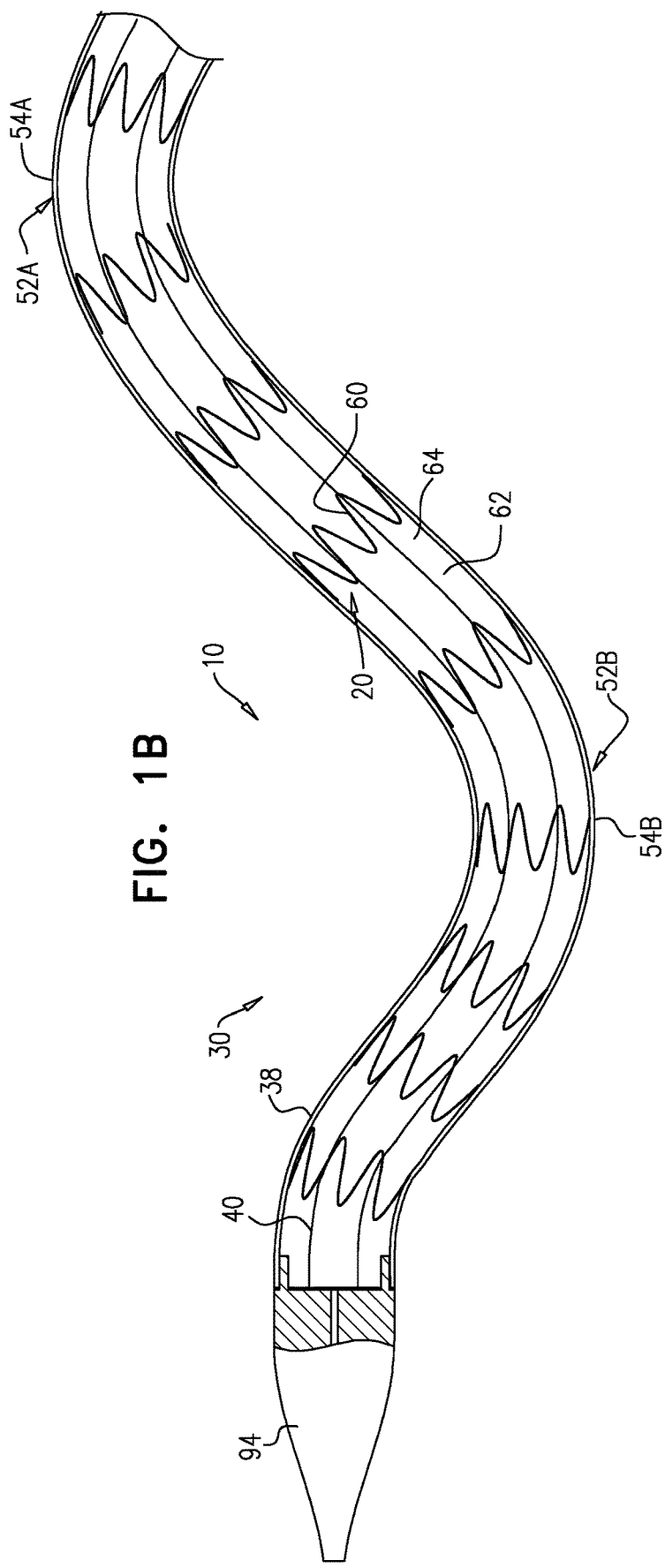
Figure 1C:
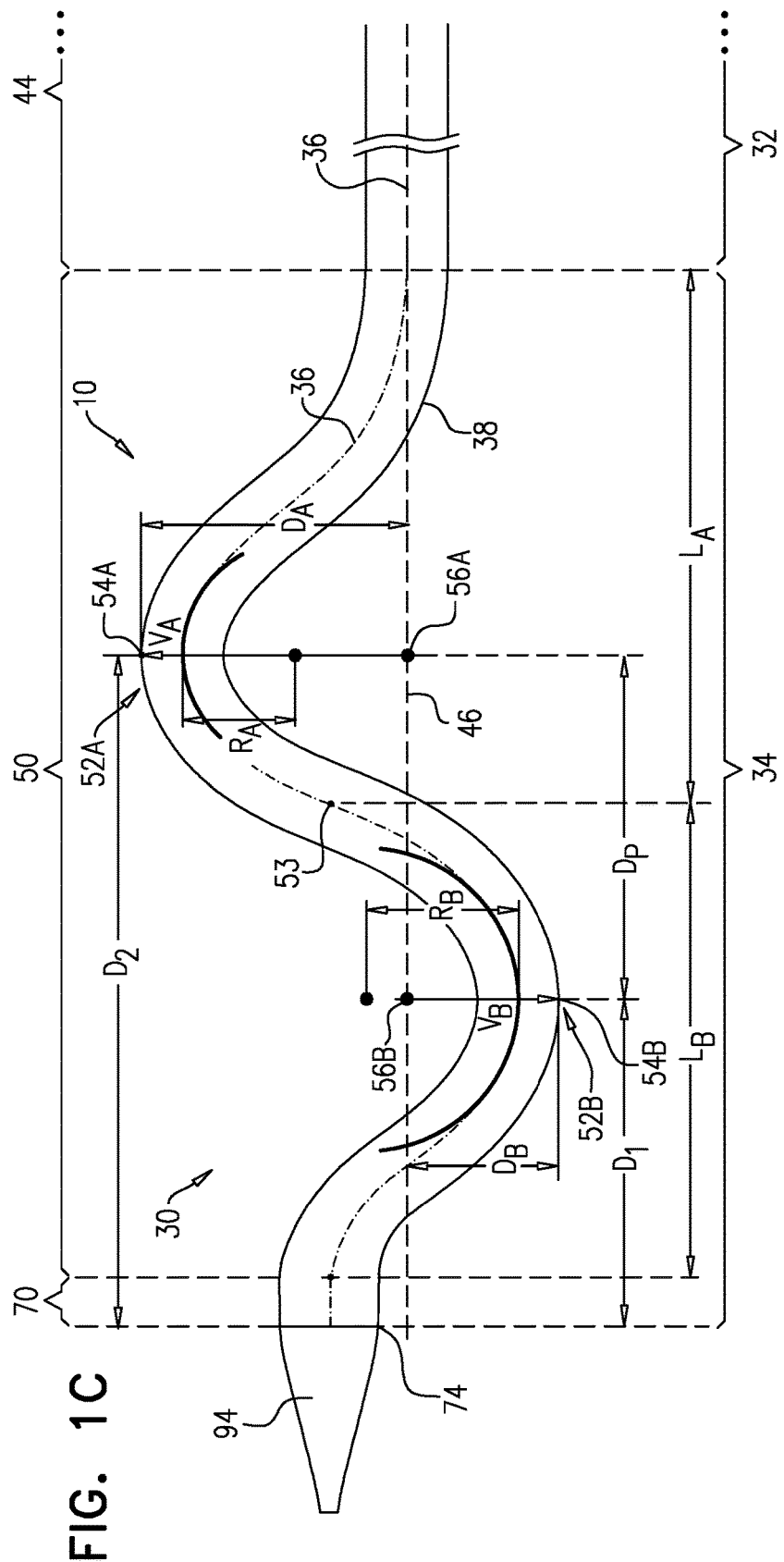
Figure 1D:
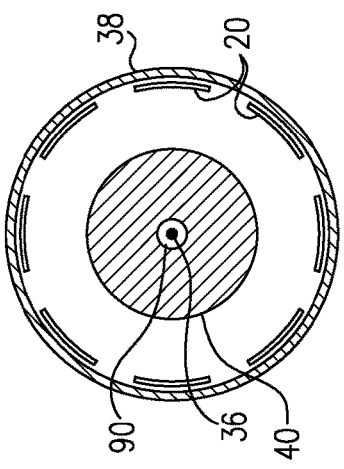

FIGS. 1A-D are schematic illustrations of an endovascular system 10, in accordance with an application of the present invention. FIG. 1B is a cross-sectional view taken along line IB-IB of FIG. 1A, and FIG. 1D is a cross-sectional view taken along line ID-ID of FIG. 1A. Endovascular system 10 comprises a stent-graft 20 and an elongate delivery shaft assembly 30. Stent-graft 20 is configured to transition from a radially-compressed delivery state to a radially-expanded state (which is typically a relaxed state). Delivery shaft assembly 30 has proximal and distal end portions 32 and 34, defines a central longitudinal axis 36, and comprises an outer covering shaft 38 and an inner support shaft 40.

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.) The central longitudinal axis of a curved elongate structure, such as self-orienting portion 50 (described hereinbelow) is curved, rather than straight. As used in the present application, including in the claims, "proximal" means closer to a user end of the system, and "distal" means farther from the user end of the system.

FIGS. 1A-D show endovascular system 10 when delivery shaft assembly 30 is unconstrained and stent-graft 20 is removably constrained in the radially-compressed delivery state along distal end portion 34 of delivery shaft assembly 30, radially between outer covering shaft 38 and inner support shaft 40 (this state is referred to herein as the "unconstrained stent-graft-containing state" of delivery shaft assembly 30). Delivery shaft assembly 30 is "unconstrained" when no constraining forces are applied to the delivery shaft assembly by a deployment tool (such as an external delivery catheter in which delivery shaft assembly 30 is disposed, and/or a tensioned guidewire, which is disposed within inner support shaft 40) or anatomy of the subject (such as the wall of a blood vessel, e.g., the aorta): delivery shaft assembly 30 is "unconstrained" even though stent-graft 20 is disposed therein.

When delivery shaft assembly 30 is unconstrained and stent-graft 20 is removably constrained in the radially-compressed delivery state along distal end portion 34 of delivery shaft assembly 30, radially between outer covering shaft 38 and inner support shaft 40, such as shown in FIGS. 1A-D, delivery shaft assembly 30 is shaped so as to define a self-orienting portion 50, and, typically, a proximal straight portion 44 disposed more proximal than self-orienting portion 50. For some applications (as shown), distal end portion 34 of delivery shaft assembly 30 is shaped so as to define self-orienting portion 50. Central longitudinal axis 36 of delivery shaft assembly 30 along proximal straight portion 44 defines a straight axis line 46 (which extends to infinity). Proximal straight portion 44 typically has a length of at least 50 cm.

When delivery shaft assembly 30 is in the unconstrained stent-graft-containing state, self-orienting portion 50 is shaped so as to define:
  at least proximal and distal curved portions 52A and 52B:
    proximal curved portion 52A is disposed more proximal than distal curved portion 52B, and
  at least one point of inflection 53 on central longitudinal axis 36 longitudinally between proximal and distal curved portions 52A and 52B.

When delivery shaft assembly 30 is in the unconstrained stent-graft-containing state, typically respective smallest radii of curvature $R_A$ and $R_B$ of proximal and distal curved portions 52A and 52B, measured at central longitudinal axis 36, are each at least 2.5 cm, no more than 12 cm, and/or between 2.5 and 12 cm, e.g., at least 4 cm, no more than 10 cm, and/or between 4 and 10 cm, as labeled in FIG. 1C.

When delivery shaft assembly 30 is in the unconstrained stent-graft-containing state, proximal and distal curved portions 52A and 52B have respective proximal and distal peaks 54A and 54B with respect to straight axis line 46, so as to define proximal and distal vectors $V_A$ and $V_B$ that:
  have respective origins 56A and 56B on straight axis line 46,
  are perpendicular to straight axis line 46, and
  intersect proximal and distal peaks 54A and 54B, respectively.

Typically, respective radii of curvature $R_A$ and $R_B$ of self-orienting portion 50, measured at central longitudinal axis 36, longitudinally at proximal and distal peaks 54A and 54B, are each at least 2.5 cm, no more than 12 cm, and/or between 2.5 and 12 cm, e.g., at least 4 cm, no more than 10 cm, and/or between 4 and 10 cm, as labeled in FIG. 1C. As used in the present application, including in the claims, a peak of a curve with respect to a straight axis line is the point on the curve that is farthest from the straight axis line, measured perpendicular to the straight axis line.

As described in more detail hereinbelow with reference to FIGS. 3A-B, an angle α (alpha) between the proximal and the distal vectors is typically at least 120 degrees, such as at least 150 degrees, e.g., 180 degrees (as shown in FIGS. 1A-C). Typically, the curved shape of self-orienting portion 50 is provided by outer covering shaft 38. Alternatively or additionally, the curved shape of self-orienting portion 50 is provided by inner support shaft 40.

Stent-graft 20 comprises a plurality of structural strut members 60, and a graft member 62. Typically, structural strut members 60 comprise a metal, such as a flexible metal, an elastic metal, stainless steel, or a superelastic alloy (such as Nitinol). Graft member 62 comprises one or more biologically-compatible substantially blood-impervious floppy sheets 64, which may be arranged, for example, as a cylinder, and is attached (such as by stitching) to at least a portion of structural strut members 60, on either side of the surfaces defined by the strut members, so as to define at least a main lumen when the stent-graft graft is in the radially-expanded state. The flexible sheets may comprise, for example, a polymeric material (e.g., a polyester, or polytetrafluoroethylene), a textile material (e.g., polyethylene terephthalate (PET), or expanded polytetrafluoroethylene (ePTFE)), natural tissue (e.g., saphenous vein or collagen), or a combination thereof. Typically, stent-graft 20 is shaped so as to define one or more lateral openings (such as described hereinbelow with reference to FIGS. 5C-D).

For some applications, outer covering shaft 38 comprises polyether block amide (PEBA) (commercially available as Pebax® (the Arkema Group, France)). Alternatively or additionally, for some applications, inner support shaft 40 comprises polyether ether ketone (PEEK).

For some applications, at least 70% of a total length of stent-graft 20 axially overlaps self-orienting portion 50 of delivery shaft assembly 30, when stent-graft 20 is removably constrained in the radially-compressed delivery state along distal end portion 34 of delivery shaft assembly 30, radially between outer covering shaft 38 and inner support shaft 40. The total length of stent-graft 20 is measured along central longitudinal axis 36 of self-orienting portion 50, rather than along straight axis line 46.

For some applications, proximal and distal curved portions 52A and 52B together define a sinusoid, i.e., are sinusoidal: for other applications, the curved portions are together serpentine. For some applications, proximal and distal curved portions 52A and 52B have a same curve shape, and, optionally, are of the same size. Alternatively, proximal and distal curved portions 52A and 52B are of different sizes, as shown in the figures.

For some applications, as labeled in FIG. 1C, respective distances DA and DB between (a) straight axis line 46 and (b) proximal and distal peaks 54A and 54B are each at least 3 cm, no more than 10 cm, and/or between 3 and 10 cm, when delivery shaft assembly 30 is in the unconstrained stent-graft-containing state.

For some applications, delivery shaft assembly 30 (e.g., self-orienting portion 50) is shaped so as to define one or more additional curved portions having the properties described herein. For example, such one or more additional curved portions may be disposed more distal than distal curved portion 52B, more proximal than proximal curved portion 52A, and/or longitudinally between proximal and distal curved portions 52A and 52B. Thus distal curved portion 52B is not necessarily a distal-most curved portion of delivery shaft assembly 30, and proximal curved portion 52A is not necessarily a proximal-most curved portion of delivery shaft assembly 30. For some applications, delivery shaft assembly 30 is shaped so as not to define an additional curved portion, in addition to proximal and distal curved portions 52A and 52B, having a smallest radius of curvature, measured at the central longitudinal axis, of between 2.5 and 12 cm. For some applications, delivery shaft assembly 30 is shaped so as not to define an additional curved portion, in addition to proximal and distal curved portions 52A and 52B, having a distance between straight axis line 46 and a peak of the additional curved portion of at least 3 cm.

For some applications, delivery shaft assembly 30 is further shaped so as to define a distal straight portion 70 which is disposed distal to self-orienting portion 50, when delivery shaft assembly 30 is in the unconstrained stent-graft-containing state. For some applications, distal straight portion 70 has a length of at least 10 mm, and/or a length equal to at least 10% of a length of stent-graft 20 (measured along central longitudinal axis 36 of self-orienting portion 50, rather than along straight axis line 46).

Proximal and distal curved portions 52A and 52B have respective axial lengths $L_A$ and $L_B$ (labeled in FIG. 1C), measured parallel to straight axis line 46, when delivery shaft assembly 30 is in the unconstrained stent-graft-containing state. The proximal and distal ends of each of the curved portions are defined by the respective points on central longitudinal axis 36 at which the central longitudinal axis is no longer curved, or transitions from the curvature of the proximal curved portion to that of the distal curved portion (i.e., point of inflection 53). For some applications, axial lengths $L_A$ and $L_B$ are each at least 4 cm, no more than 18 cm, and/or between 4 and 18 cm, and/or are each at least 25%, no more than 125%, and/or between 25% and 125% of a length of stent-graft 20 (measured along central longitudinal axis 36 of self-orienting portion 50, rather than along straight axis line 46). For some applications, a sum of axial lengths $L_A$ and $L_B$ is at least 8 cm, no more than 36 cm, and/or between 8 and 36 cm, and/or at least 50%, no more than 150%, and/or between 50% and 150% of the length of stent-graft 20.

For some applications, a distance $D_P$ between proximal and distal peaks 54A and 54B (labeled in FIG. 1C), measured parallel to straight axis line 46, is at least 5 cm, no more than 20 cm, and/or between 5 and 20 cm, and/or at least 50%, no more than 120%, and/or between 50% and 120% of the length of stent-graft 20, as defined above, when delivery shaft assembly 30 is in the unconstrained stent-graft-containing state.

For some applications, a distance $D_1$ between distal peak 54B and a distal end 74 of outer covering shaft 38 (labeled in FIG. 1C), measured parallel to straight axis line 46, is at least 3 cm, no more than 8 cm, and/or between 3 and 8 cm, and/or at least 15%, no more than 40%, and/or between 15% and 40% of the length of stent-graft 20, as defined above, when delivery shaft assembly 30 is in the unconstrained stent-graft-containing state.

For some applications, a distance $D_2$ between proximal peak 54A and distal end 74 of outer covering shaft 38, measured parallel to straight axis line 46, is at least 5 cm, no more than 30 cm, and/or between 5 and 30 cm, and/or at least 25%, no more than 125%, and/or between 25% and 125% of the length of stent-graft 20, as defined above, when delivery shaft assembly 30 is in the unconstrained stent-graft-containing state, as labeled in FIG. 1C.

For some applications, a distance between proximal peak 54A and a proximal end of outer covering shaft 38 (labeled in FIG. 1C), measured parallel to straight axis line 46, is at least 50 cm, no more than 120 cm, and/or between 50 and 120 cm, when delivery shaft assembly 30 is in the unconstrained stent-graft-containing state.

Reference is again made to FIG. 1A. For some applications, endovascular system 10 further comprises a user handle 80, which is fixed to outer covering shaft 38 and inner support shaft 40 at a proximal shaft end 82 of delivery shaft assembly 30, and is configured to effect longitudinal displacement between outer covering shaft 38 and inner support shaft 40, thereby releasing stent-graft 20 from delivery shaft assembly 30, and allowing stent-graft 20 to transition from the radially-compressed delivery state to the radially-expanded state.

Typically, inner support shaft 40 is shaped so as to define at least one internal bore 90, which is sized for passage therethrough of a guidewire 92, as is known in the stent-graft deployment art. For some applications, endovascular system 10 further comprises a distal tip 94, which is fixed to and extends distally beyond a distal end of inner support shaft 40. Typically, distal tip 94 is conical.

Figure 2A:
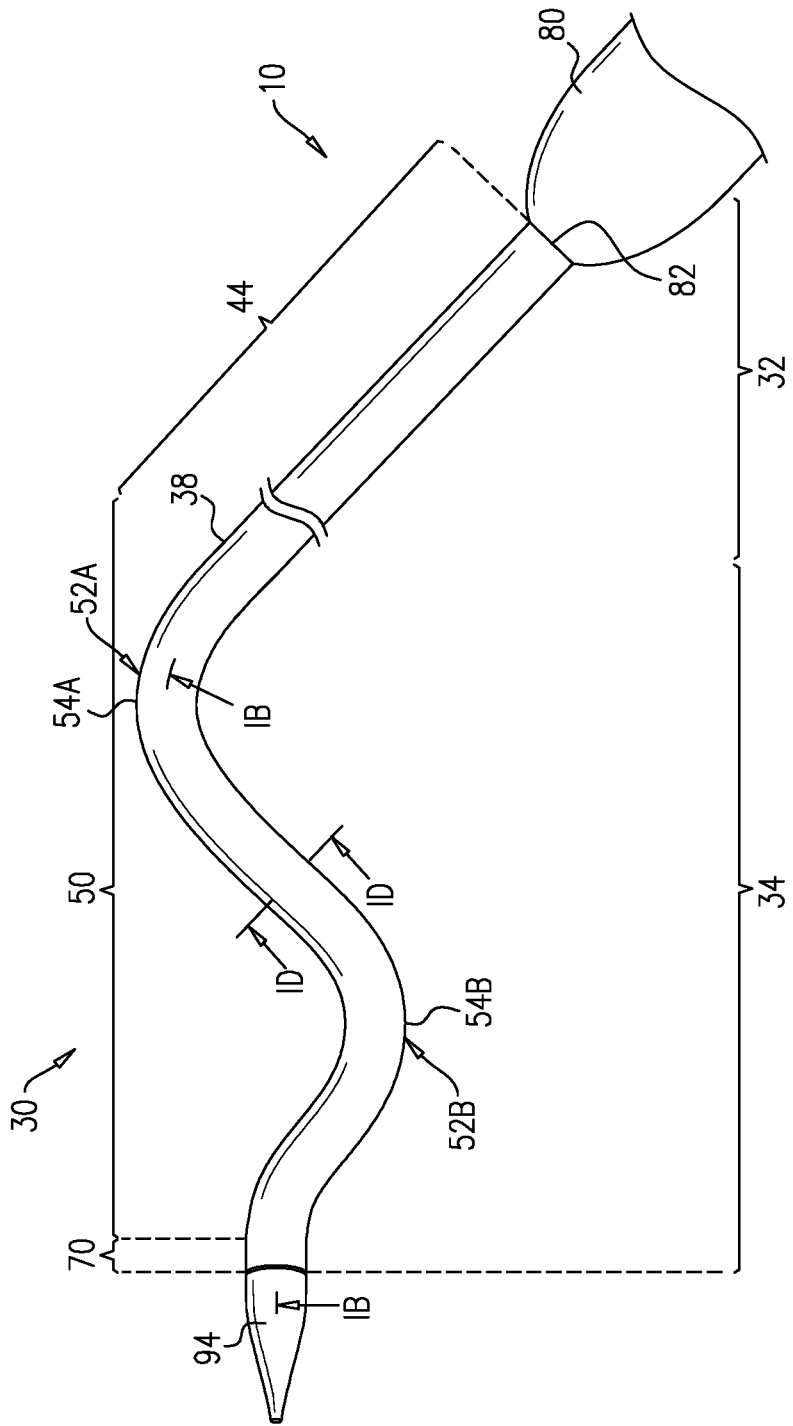
FIGS. 2A-B are schematic illustrations of an alternate configuration of the endovascular system of FIGS. 1A-D, in accordance with an application of the present invention.
Figure 2B:
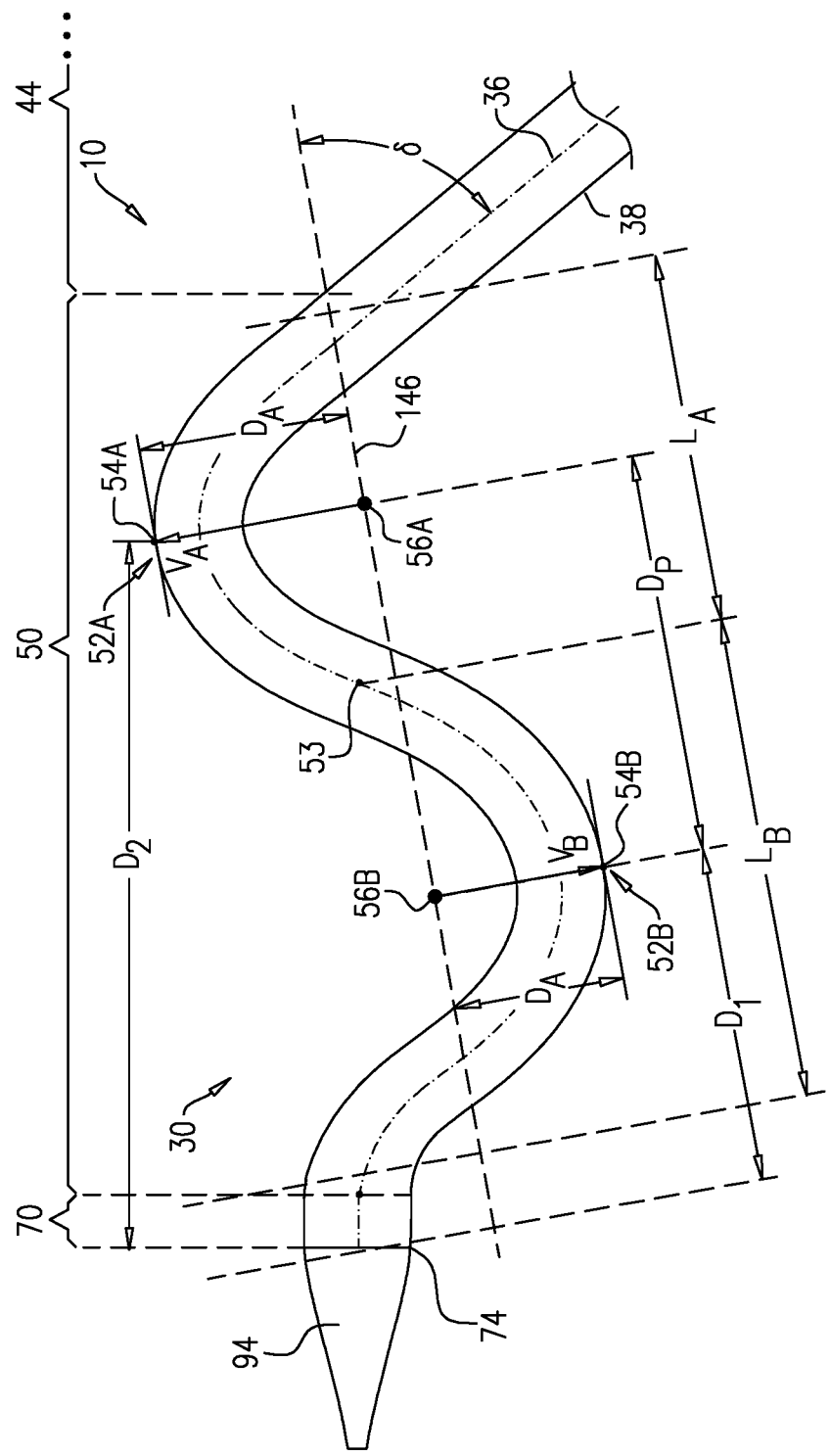

Reference is now made to FIGS. 2A-B, which are schematic illustrations of another configuration of endovascular system 10, in accordance with an application of the present invention. In the configuration shown in FIGS. 2A-B (as well as in the configuration shown in FIGS. 1A-D and in other configurations not shown), self-orienting portion 50 of endovascular system 10 defines a best-fit straight axis line 146 that best matches proximal and distal curved portions 52A and 52B, i.e., that has a minimum sum of squares of distances between best-fit straight axis line 146 and central longitudinal axis 36 along proximal and distal curved portions 52A and 52B. (As mentioned above, central longitudinal axis 36 is curved along these portions.) Methods for calculating the minimum sum of squares are well known in mathematics. For some applications, an angle δ (delta) between best-fit straight axis line 146 and central longitudinal axis 36 along proximal straight portion 44 is at least 10 degrees, no more than 60 degrees, and/or between 10 and 60 degrees.

All of the properties of self-orienting portion 50 described hereinabove with reference to FIGS. 1A-D, which relate to straight axis line 46, are also applicable to self-orienting portion 50, and instead relate to best-fit straight axis line 146. For example, proximal and distal peaks 54A and 54B of proximal and distal curved portions 52A and 52B are with respect to best-fit straight axis line 146. Also for example, when delivery shaft assembly 30 is in the unconstrained stent-graft-containing state, (a) proximal and distal peaks 54A and 54B define respective proximal and distal vectors $V_A$ and $V_B$, which (i) have respective origins 56A and 56B on best-fit straight axis line 146, (ii) are perpendicular to best-fit straight axis line 146, and (iii) intersect proximal and distal peaks 54A and 54B, respectively, and (b) angle α (alpha) between proximal and distal vectors $V_A$ and $V_B$ is at least 120 degrees, such as at least 150 degrees, e.g., 180 degrees (as shown in FIGS. 2A-B).

Figure 3A:
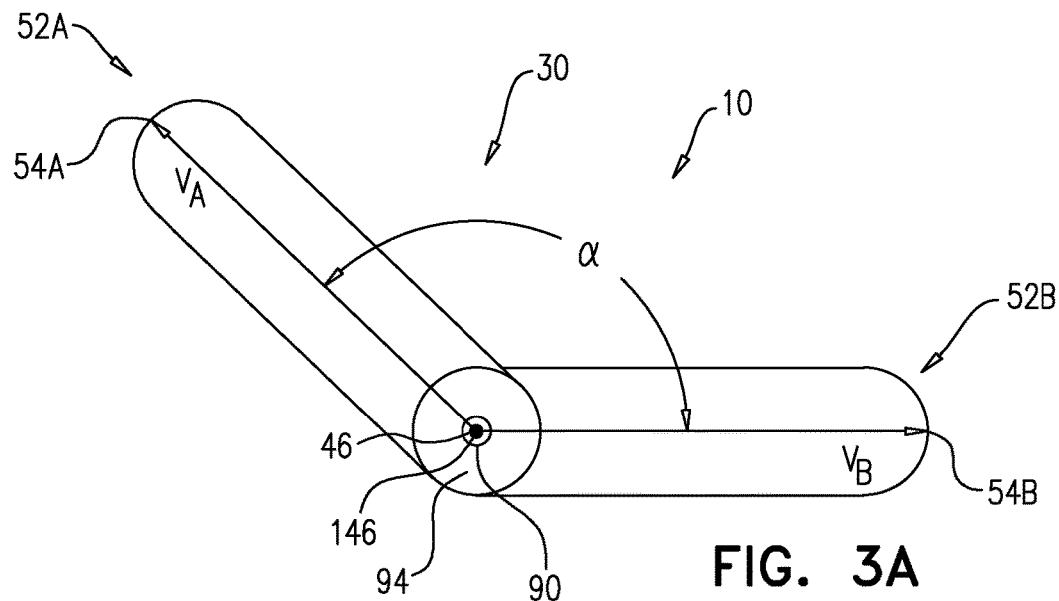
FIGS. 3A-B are schematic illustrations of two configurations of the endovascular system of FIGS. 1A-D and 2A-B, in accordance with respective applications of the present invention.
Figure 3B:
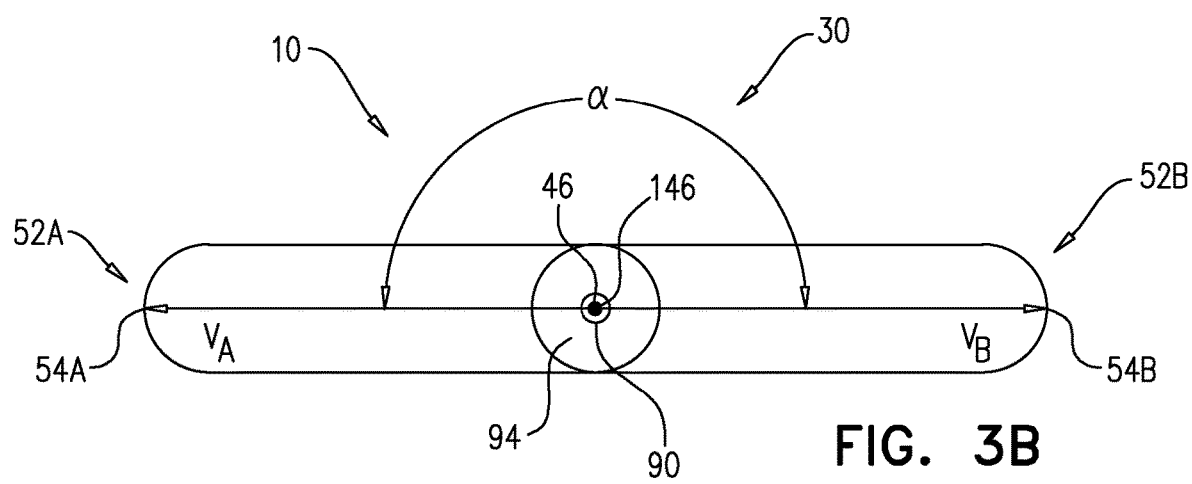

Reference is now made to FIGS. 3A-B, which are schematic illustrations of two configurations of endovascular system 10, in accordance with respective applications of the present invention. FIGS. 3A-B are views of elongate delivery shaft assembly 30 from a distal perspective, as if a viewer were looking straight-on at distal tip 94. As described hereinabove with reference to FIGS. 1A-D, angle α (alpha) between proximal and distal vectors $V_A$ and $V_B$ is typically at least 120 degrees, such as shown in FIG. 3A, e.g., 180 degrees, such as shown in FIG. 3B. (It is noted that in FIGS.

3A-B, unlike in FIGS. 1A and 1C, distal tip 94 is coaxial with straight axis line 46 (FIGS. 1A-D) or best-fit straight axis line 146 (FIGS. 2A-B).)

Figure 4:
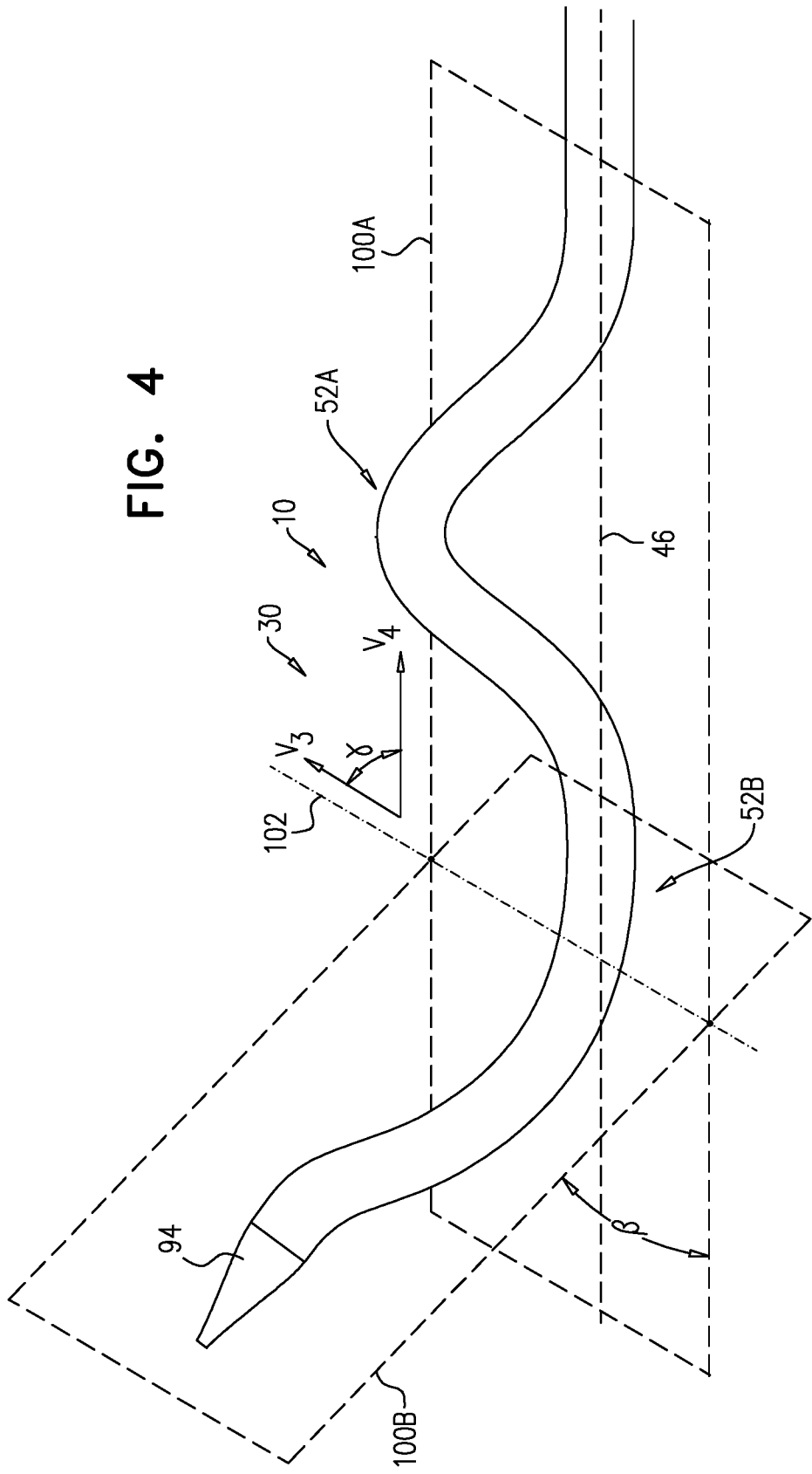
FIG. 4 is a schematic illustration of another configuration of the endovascular system of FIGS. 1A-D, in accordance with an application of the present invention.

Reference is now made to FIG. 4, which is a schematic illustration of another configuration of endovascular system 10, in accordance with an application of the present invention. For some applications, when delivery shaft assembly 30 is in the unconstrained stent-graft-containing state, radially between outer covering shaft 38 and inner support shaft 40:

proximal and distal curved portions 52A and 52B define respective proximal and distal best-fit planes 100A and 100B, an angle β (beta) between proximal and distal best-fit planes 100A and 100B is no more than 60 degrees, such as no more than 40 degrees, and/or at least 30 degrees, and proximal and distal best-fit planes 100A and 100B intersect at an intersection line 102 that is not parallel to straight axis line 46.

For some applications, (a) a third vector $V_3$ parallel to intersection line 102 and (b) a fourth vector $V_4$ parallel to straight axis line 46 form an angle γ (gamma) of between 30 and 90 degrees, such as between 60 and 90 degrees.

As used in the present application, including in the claims, a "best-fit plane" is the plane that most closely matches the spatial curvature of central longitudinal axis 36 along a given curved portion, i.e., the plane that results in the minimal sum of squares of distances between the plane and central longitudinal axis 36 of the curved portion. As used in the present application, including in the claims, an angle between two lines or two planes (but not two vectors) is the smaller of the two supplementary angles between the two lines or two planes, or equals 90 degrees if the two lines or two planes are perpendicular.

Reference is now made to FIGS. 5A-D, which are schematic illustrations of an exemplary transvascular delivery procedure for deploying stent-graft 20 in an aortic arch 200 using endovascular system 10, in accordance with an application of the present invention. FIGS. 5A-D schematically show a portion of a typical aorta, including a thoracic aorta, which includes an upper part of an ascending aorta 201, aortic arch 200, and an upper part of a supra-renal descending aorta 202. Also shown are the three branches of aortic arch 200: a brachiocephalic artery 203, a left common carotid artery 204, and a left subclavian artery 205. In addition, left and right renal arteries 206 and 207 are shown. Stent-graft 20 may be used to treat a blood vessel, such as aortic arch 200, suffering from an aneurysm, a dissection, or, more generally, a pathologically dilated aorta. Although FIGS. 5A-D illustrate the deployment using the configuration of delivery shaft assembly 30 shown in FIGS. 1A-D, the configuration of the delivery shaft assembly shown in FIGS. 2A-B may be similarly used.

In the particular configuration described with reference to FIGS. 5A-D, and shown in FIGS. 5C-D, stent-graft 20 is in some respects similar to, and may implement any or all of the features of first stent-graft 20, described with reference to FIGS. 4-6H and/or FIG. 7 of PCT Publication WO 2011/064782, which is incorporated herein by reference. In particular, when in the radially-expanded state, stent-graft 20 may be shaped so as to define a superior lateral opening 230 and an inferior lateral opening 232. (Optionally, superior lateral opening 230 is a distal superior lateral opening, and the stent-graft is shaped so as to further define a proximal superior lateral opening, such as described with reference to FIGS. 4-6H in the '782 publication.) Typically, at least when stent-graft 20 is unconstrained in the radially-expanded state, superior lateral opening 230 faces in a first radial direction, and inferior lateral opening 232 faces in a second radially direction generally circumferentially opposite the first radial direction. For example, if the stent-graft is viewed from one end, superior lateral opening 230 may be disposed at between 11 o'clock and 1 o'clock (e.g., at 12 o'clock), and inferior lateral opening 232 may be disposed at between 5 o'clock and 7 o'clock (e.g., at 6 o'clock).

Typically, when delivery shaft assembly 30 is in the unconstrained stent-graft-containing state, stent-graft 20 is rotationally, and, optionally, axially, disposed in delivery shaft assembly 30 such that, upon deployment therefrom, superior lateral opening 230 is rotationally, and, optionally, axially, aligned with left common carotid artery 204, as described hereinbelow with reference to FIG. 5C. To this end:

when delivery shaft assembly 30 is in the unconstrained stent-graft-containing state, stent-graft 20 is typically axially disposed in delivery shaft assembly 30 such that superior lateral opening 230 is in self-orienting portion 50, and when delivery shaft assembly 30 is in the unconstrained stent-graft-containing state, stent-graft 20 is rotationally oriented with respect to delivery shaft assembly 30 so as to, upon release of the stent-graft from delivery shaft assembly 30 without rotation of the stent-graft, define a shortest line between (a) central longitudinal axis 36 and (b) a centroid of superior lateral opening 230 parallel to central longitudinal axis 36. The shortest line is typically perpendicular to central longitudinal axis 36, and forms an angle of no more than 30 degrees, e.g., no more than 15 degrees, with proximal best-fit plane 100A. The plane is defined when delivery shaft assembly 30 is in the unconstrained stent-graft-containing state. For example, the line may be parallel to proximal best-fit plane 100A, e.g., may be in proximal best-fit plane 100A. As used in the present application, including in the claims, a "centroid" of superior lateral opening 230 is the arithmetic mean position of all the points in the superior lateral opening, as defined by the border around the opening.

Figure 5A:
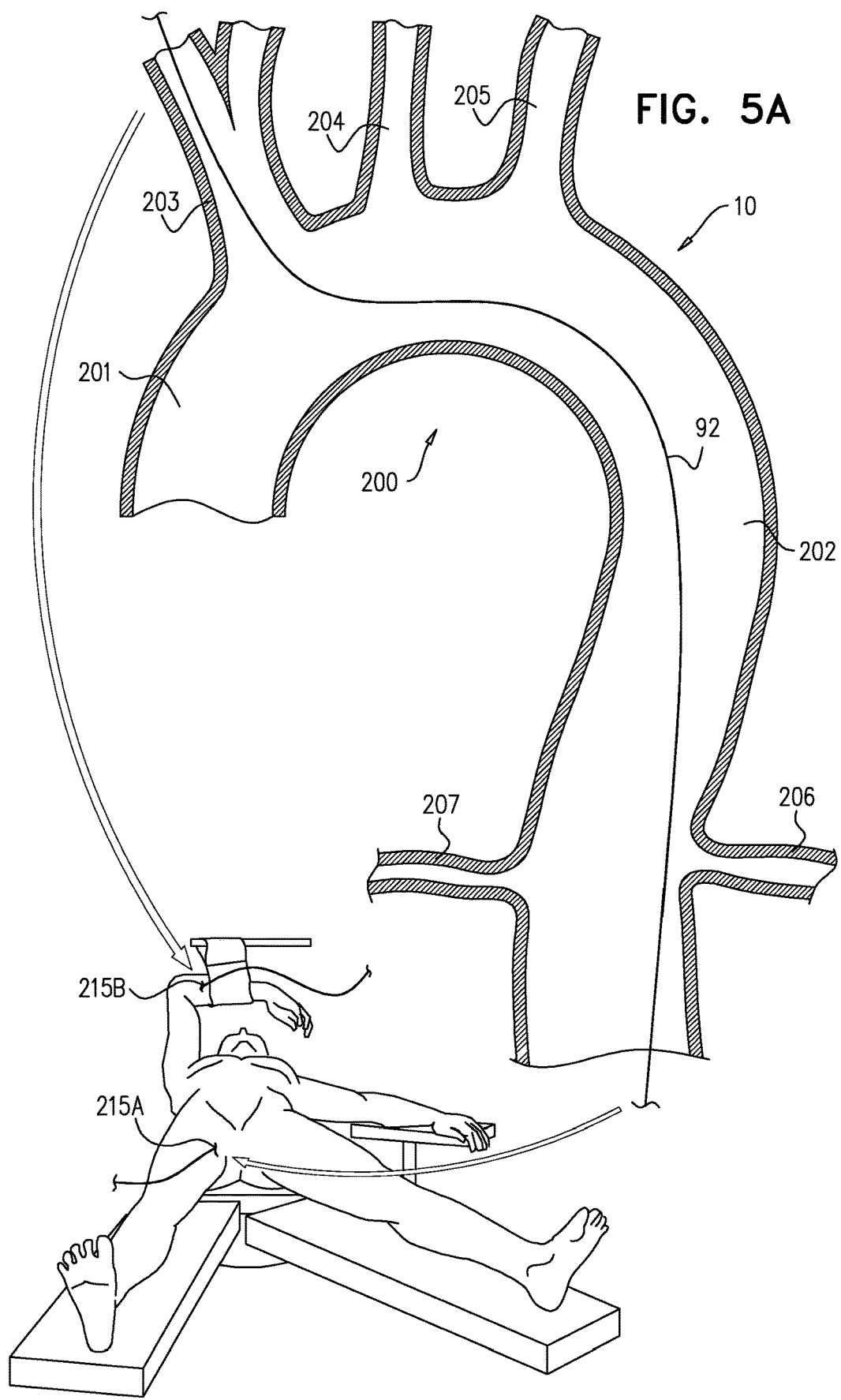
FIGS. 5A-D are schematic illustrations of an exemplary transvascular delivery procedure for a deploying stent-graft of the endovascular system of FIGS. 1A-D in an aortic arch using the endovascular system, in accordance with an application of the present invention.

As shown in FIG. 5A, during a first stage of the implantation procedure, guidewire 92 of endovascular system 10 is endovascularly (preferably percutaneously) introduced into the vasculature at a first vascular access site 215A, advanced through the vasculature, and extracted from the vasculature and the patient's body at a second vascular access site 215B different from the first, such that the guidewire extends between two vascular access sites through the vasculature. In the exemplary method illustrated in FIGS. 5A-D, the guidewire is introduced into aortic arch 200 via one of the iliac arteries through first vascular access site 215A, such as on the right femoral artery or the right iliac artery. The guidewire is advanced up descending aorta 202 and into a first one of the branches of the aortic arch, such as a brachiocephalic artery 203, and extracted from the vasculature and the patient's body through second vascular access site 215B, such as on the brachial artery. For example, the operator may draw the distal end of the guidewire out through the second vascular access site using a lasso introduced to the vasculature through the second vascular access site, or using an introducer sheath introduced to the vasculature through the second vascular access site (for example, the introducer sheath may have a diameter about equal to blood vessels as the introducer sheath narrows at the end thereof distal to the user, and the operator may radiographically introduce the guidewire into the sheath). Optionally, endovascular system 10 implements the distal restraining assembly described in PCT Publication WO 2014/108895, which is incorporated herein by reference.

Figure 5B:
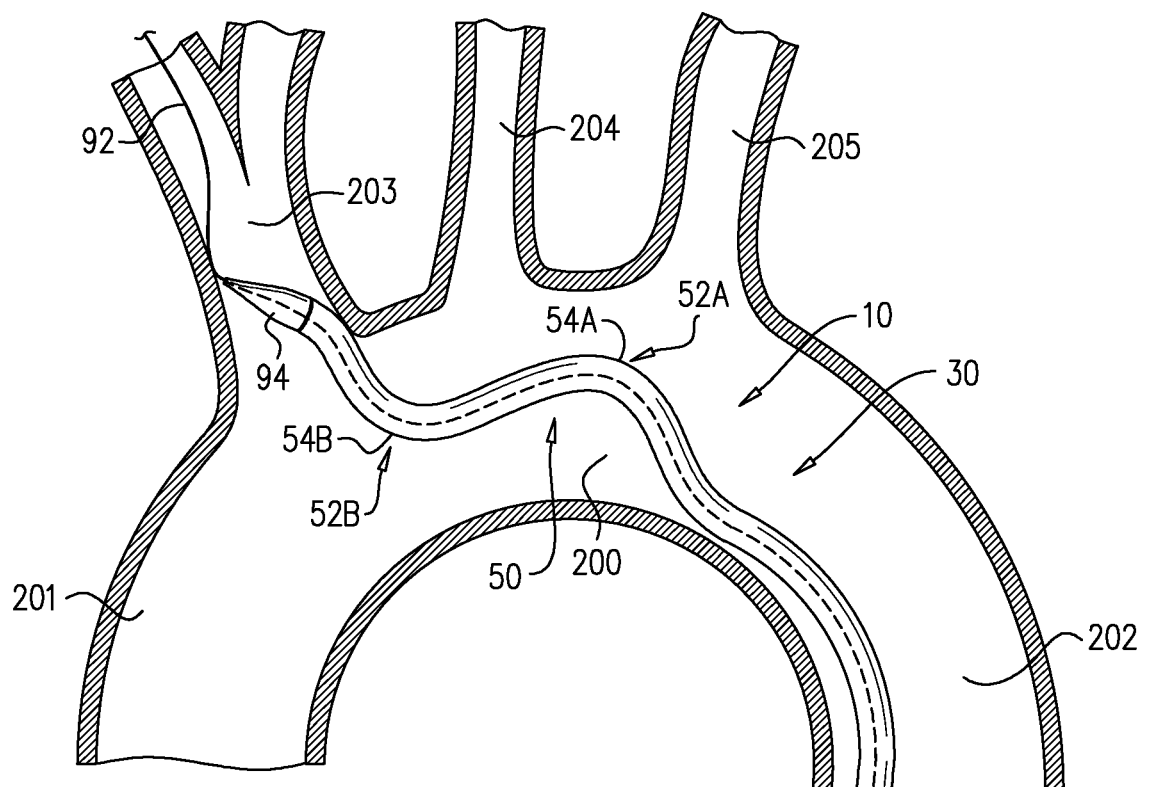

As shown in FIG. 5B, elongate delivery shaft assembly 30 is advanced over guidewire 92, while stent-graft 20 is removably constrained in the radially-compressed delivery state along distal end portion 34 of delivery shaft assembly 30, radially between outer covering shaft 38 and inner support shaft 40, until stent-graft 20 is partially disposed in brachiocephalic artery 203, partially disposed in aortic arch 200, and partially disposed in an upper part of descending aorta 202. Optionally, if necessary for navigation through the vasculature, self-orienting portion 50 may be at least partially constrained to a straight configuration by tensioning guidewire 92 from its ends outside the body, and/or by introducing the self-orienting portion inside an external delivery catheter 220. Once delivery shaft assembly 30 approaches the desired location in the vasculature, the tension on the guidewire may be temporarily released so as to allow delivery shaft assembly 30 to assume its precurved shape and hence effect its self-orientation relative to the target vascular anatomy, and/or external delivery catheter 220 is withdrawn.

As shown in FIG. 5B, self-orienting portion 50 automatically rotationally orients itself to a least constrained state, i.e., to an orientation in which the wall of aortic arch 200 applies the least force to self-orienting portion 50. As a result, proximal curved portion 52A faces in a superior direction (in a direction generally toward left common carotid artery 204 and a left subclavian artery 205), and distal curved portion 52B faces in an inferior direction (in an upstream direction toward ascending aorta 201). In addition, superior lateral opening 230 is rotationally aligned with left common carotid artery 204, as described above. Therefore, manual rotation of delivery shaft assembly 30 is generally not necessary. Proximal end portion 32 is typically quite long (e.g., between 50 and 120 cm), and thus transmits proximal torque poorly to distal end portion 34. As a result, manual rotation of delivery shaft assembly 30 is often difficult or impossible, and/or may result in damage to the delivery shaft assembly, or in an unexpected rotation of the stent-graft, because of the rotational static torque accumulated in the delivery system during rotation thereof at user handle 80. In addition, it is generally difficult, if not impossible, to properly rotationally orient delivery shaft assembly 30 before and/or during introduction into the vasculature, because the tortuous vasculature changes the rotation of the delivery shaft assembly as it is advanced. The axial position of delivery shaft assembly 30 may be adjusted if necessary to axially align superior lateral opening 230 with left common carotid artery 204.

Figure 5C:
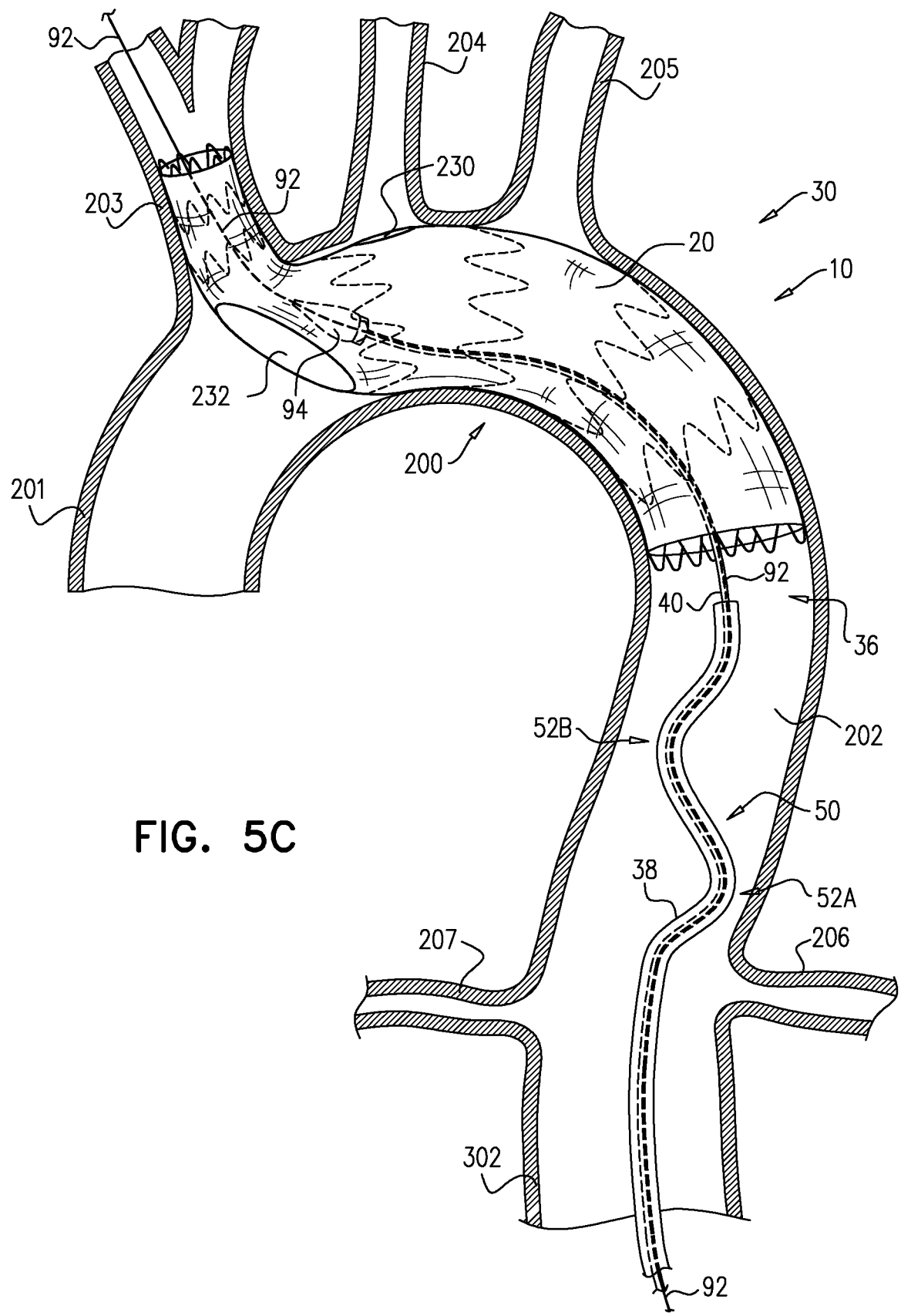

As shown in FIG. 5C, outer covering shaft 38 of delivery shaft assembly 30 is proximally withdrawn while stent-graft 20 and inner support shaft 40 are held in place, releasing stent-graft 20 in the vasculature. Stent-graft 20 radially expands and transitions to the radially-expanded deployment state as it is released. FIG. 5C shows the stent-graft fully released from the outer covering shaft.

Figure 5D:
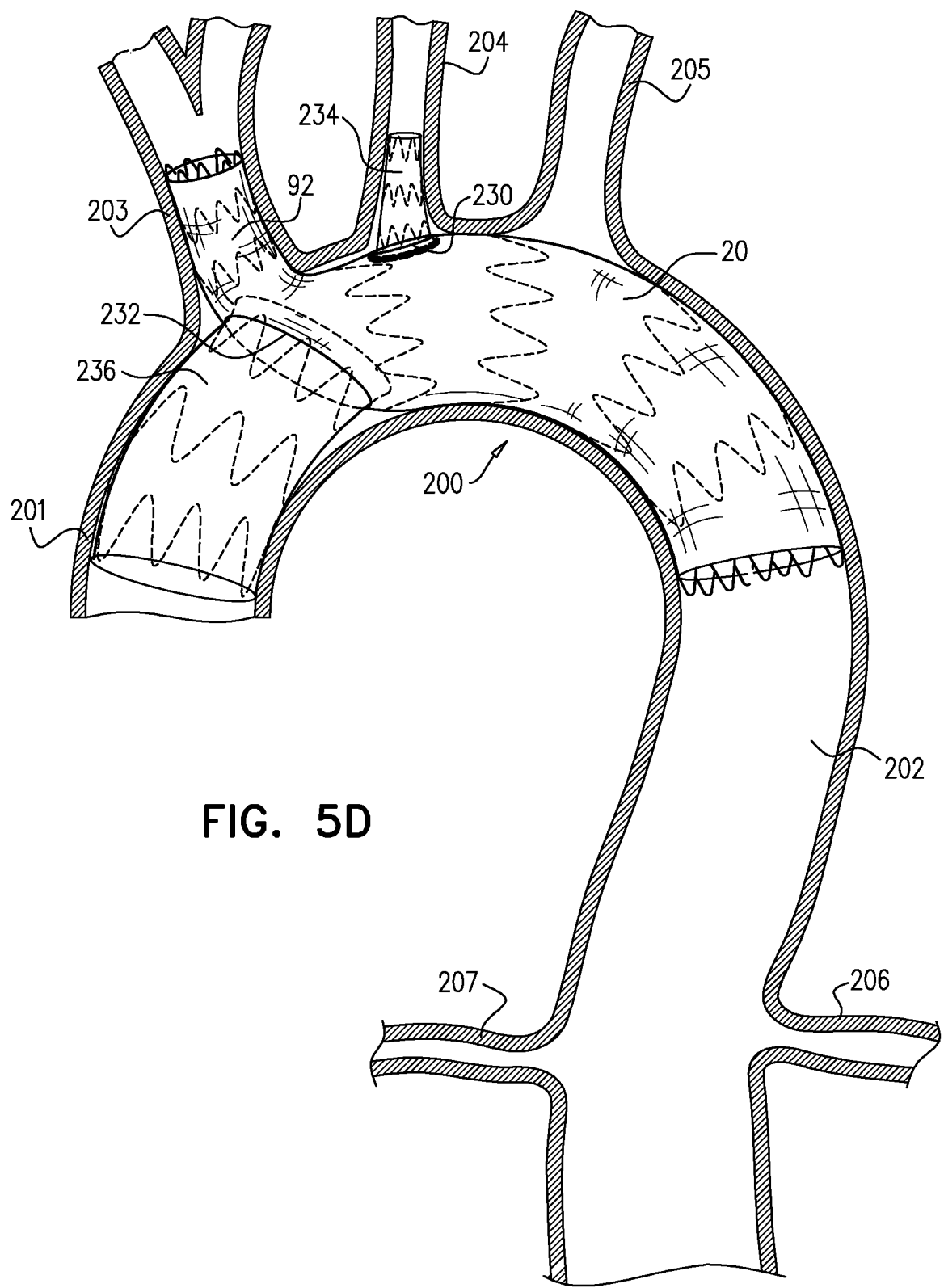

FIG. 5D shows stent-graft 20 after delivery shaft assembly 30 has been fully withdrawn from the patient's vasculature. In the exemplary deployment illustrated in FIG. 5D, a proximal portion of stent-graft 20, including a proximal end thereof, is positioned in the upper part of descending aorta 202, a middle portion of stent-graft 20 is positioned in aortic arch 200, and a distal portion of stent-graft 20, including a distal end thereof, is positioned in brachiocephalic artery 203. Superior lateral opening 230 faces toward and is aligned with a left subclavian artery 205, and inferior lateral opening 232 is disposed in aortic arch 200 facing upstream, generally toward ascending aorta 201, in a vicinity of the bifurcation of aortic arch 200 and brachiocephalic artery 203.

FIG. 5D also shows stent-graft 20 after the subsequent deployment of two second endovascular stent-grafts 234 and 236, which, together with stent-graft 20, are components of a multi-component stent-graft system. These two second endovascular stent-grafts are typically deployed using one or more guidewires and delivery shafts separate from guidewire 92 and delivery shaft assembly 30. In the illustrated deployment, these two second endovascular stent-grafts comprise:

second endovascular stent-graft 234, which is deployed up descending aorta 202, through a proximal portion of stent-graft 20, partially out of superior lateral opening 230 so as to form a blood-tight seal with the lateral opening, and into left common carotid artery 304, such as described with reference to FIGS. 6E-F of the above-references '782 publication: second endovascular stent-graft 234 is thus securely deployed partially outside and partially inside superior lateral opening 230; and second endovascular stent-graft 236, which is deployed up descending aorta 302, through a proximal portion of stent-graft 20, partially out of inferior lateral opening 232 so as to form a blood-tight seal with the lateral opening, and into aortic arch 200 and/or the upper part of ascending aorta 301, such as described with reference to FIGS. 6B-D of the above-mentioned '782 publication: second endovascular stent-graft 236 is thus securely deployed partially outside and partially inside inferior lateral opening 232: optionally, second endovascular stent-graft 236 comprises the self-curving longitudinal portion described in U.S. Provisional Application No. 62/102,265, filed Jan. 12, 2015, which is assigned to the assignee of the present application and is incorporated herein by reference.

As can be seen in FIG. 5D, upon deployment of all three stent-grafts, the multi-component stent-graft system defines a blood-flow path from ascending aorta 201, over aortic arch 200, and to descending aorta 202. The multi-component stent-graft system additionally provides blood-flow paths to brachiocephalic artery 203 and left common carotid artery 204. It is noted that in the deployment shown in FIG. 5D, blood flow to left subclavian artery 205 is blocked by stent-graft 20. The left subclavian artery is either "sacrificed" (i.e. via occlusion), or surgically anastomosed to the left common carotid artery, or possibly to another source artery, such as the right common carotid artery. Alternatively, stent-graft 20 is shaped so as to define both proximal and distal superior lateral openings, such as described with reference to FIGS. 4-6H in the above-mentioned '782 publication, in which case the proximal superior lateral opening is aligned with left subclavian artery 305, and another second endovascular stent-graft is typically deployed through the proximal superior lateral opening into the left subclavian artery.

For some applications, stent-graft 20 comprises one or more fatigue-resistant lateral tubes, such as described in U.S. Provisional Application No. 62/093,497, filed Dec. 18, 2014, which is assigned to the assignee of the present application and is incorporated herein by reference. For example, stent-graft 20 may implement some or all of the features described with reference to FIG. 6B of the '497 application. The one or more fatigue-resistant lateral tubes extend from one or more of the lateral openings described above.

In an experiment conducted on behalf of the inventors, several anatomical models of the human vasculature between the internal and external iliac arteries and up to the first bifurcations on the supra-aortic vessels were manufactured using information collected from CT imaging. An endovascular system similar to endovascular system 10 was advanced through the modeled vasculature, and a stent-graft similar to stent-graft 20 was deployed. It was not necessary to rotate the delivery shaft assembly of the endovascular system in order to properly align the superior lateral opening of the stent-graft with the modeled left common carotid artery, as it self-oriented to the correct rotational configuration, while it was axially introduced into the target location, when its conical tip lay at the bifurcation of the brachiocephalic artery.

The scope of the present invention includes embodiments described in the following patents and patent applications, which are assigned to the assignee of the present application and are incorporated herein by reference. In an embodiment, techniques and apparatus described in one or more of the following patent applications are combined with techniques and apparatus described herein. In particular, the delivery systems described herein may be used to deliver the stent-grafts described in the following patent and patent applications, and deployed as described as described in the following patent and patent applications, mutatis mutandis.

- PCT Application PCT/IL2008/000287, filed Mar. 5, 2008, which published as PCT Publication WO 2008/107885
- PCT Application PCT/IB2010/052861, filed Jun. 23, 2010, which published as PCT Publication WO 2010/150208
- PCT Application PCT/IL2010/000564, filed Jul. 14, 2010, which published as PCT Publication WO 2011/007354
- PCT Application PCT/IL2010/000917, filed Nov. 4, 2010, which published as PCT Publication WO 2011/055364
- PCT Application PCT/IL2010/000999, filed Nov. 30, 2010, which published as PCT Publication WO 2011/064782
- PCT Application PCT/IL2010/001018, filed Dec. 2, 2010, which published as PCT Publication WO 2011/067764
- PCT Application PCT/IL2010/001037, filed Dec. 8, 2010, which published as PCT Publication WO 2011/070576
- PCT Application PCT/IL2011/000135, filed Feb. 8, 2011, which published as PCT Publication WO 2011/095979
- PCT Application PCT/IL2012/000060, filed Feb. 2, 2012, which published as PCT Publication WO 2012/104842
- PCT Application PCT/IL2012/000241, filed Jun. 19, 2012, which published as PCT Publication WO 2012/176187
- PCT Application PCT/IL2012/000300, filed Aug. 12, 2012, which published as PCT Publication WO 2013/030819
- U.S. Pat. No. 8,317,856 to Shalev et al.
- U.S. Pat. No. 8,574,287 to Benary et al.
- U.S. Provisional Application No. 60/892,885, filed Mar. 5, 2007
- U.S. Provisional Application No. 60/991,726, filed Dec. 2, 2007
- U.S. Provisional Application No. 61/219,758, filed Jun. 23, 2009
- U.S. Provisional Application No. 61/221,074, filed Jun. 28, 2009
- U.S. application Ser. No. 13/031,871, filed Feb. 22, 2011, which published as US Patent Application Publication 2011/0208289
- U.S. Provisional Application No. 61/496,613, filed Jun. 14, 2011
- U.S. Provisional Application No. 61/499,195, filed Jun. 21, 2011
- U.S. Provisional Application No. 61/505,132, filed Jul. 7, 2011
- U.S. Provisional Application No. 61/529,931, filed Sep. 1, 2011
- U.S. Provisional Application No. 61/553,209, filed Oct. 30, 2011
- U.S. Pat. No. 8,870,938
- U.S. application Ser. No. 13/384,075, filed Jan. 13, 2012, which published as US Patent Application Publication 2012/0179236
- U.S. application Ser. No. 13/505,996, filed May 3, 2012, which published as US Patent Application Publication 2012/0310324
- U.S. application Ser. No. 13/513,397, filed Jun. 1, 2012, which published as US Patent Application Publication 2012/0330399
- U.S. application Ser. No. 13/514,240, filed Jun. 6, 2012, which published as US Patent Application Publication 2013/0013051
- U.S. Provisional Application No. 61/678,182, filed Aug. 1, 2012
- U.S. application Ser. No. 13/577,161, filed Aug. 3, 2012, which published as US Patent Application Publication 2013/0035751
- U.S. application Ser. No. 13/512,778, filed Sep. 24, 2012, which published as US Patent Application Publication 2013/0013050
- U.S. application Ser. No. 13/807,880, filed Dec. 31, 2012, which published as US Patent Application Publication 2013/0131783
- PCT Application PCT/IL2012/000095, filed Mar. 1, 2012, which published as PCT Publication WO 2012/117395
- PCT Application PCT/IL2012/000148, filed Apr. 4, 2012, which published as PCT Publication WO 2013/030818
- PCT Application PCT/IL2012/000190, filed May 15, 2012, which published as PCT Publication WO 2013/171730
- PCT Application PCT/IL2012/000269, filed Jul. 2, 2012, which published as PCT Publication WO 2013/005207
- PCT Application PCT/IL2012/050424, filed Oct. 29, 2012, which published as PCT Publication WO 2013/065040
- PCT Application PCT/IL2012/050506, filed Dec. 4, 2012, which published as PCT Publication WO 2013/084235
- U.S. Provisional Application No. 61/749,965, filed Jan. 8, 2013
- U.S. application Ser. No. 13/807,906, filed Feb. 8, 2013, which published as US Patent Application Publication 2013/0204343
- U.S. Provisional Application No. 61/775,964, filed Mar. 11, 2013
- U.S. Provisional Application No. 61/826,544, filed May 23, 2013
- U.S. application Ser. No. 13/979,551, filed Jul. 12, 2013, which published as US Patent Application Publication 2013/0289587
- PCT Application PCT/IL2013/050656, filed Jul. 31, 2013, which published as PCT Publication WO 2014/020609
- U.S. Provisional Application No. 61/906,014, filed Nov. 19, 2013

PCT Application PCT/IL2014/050019, filed Jan. 7, 2014, which published as PCT Publication WO 2014/108895

U.S. Provisional Application No. 61/926,533, filed Jan. 13, 2014

PCT Application PCT/IL2014/050174, filed Feb. 18, 2014, which published as PCT Publication WO 2014/141232

PCT Application PCT/IL2014/050434, filed May 18, 2014, which published as PCT Publication WO 2014/188412

PCT Application PCT/IL2014/050973, filed Nov. 6, 2014, which published as PCT Publication WO 2015/075708

U.S. Provisional Application No. 62/093,497, filed Dec. 18, 2014

U.S. Provisional Application No. 62/102,265, filed Jan. 12, 2015

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular system, which comprises:
    a stent-graft, which is configured to transition from a radially-compressed delivery state to a radially-expanded state; and
    an elongate delivery shaft assembly, which has proximal and distal end portions, defines a central longitudinal axis, and comprises an outer covering shaft and an inner support shaft,
    wherein when the delivery shaft assembly is unconstrained and the stent-graft is removably constrained in the radially-compressed delivery state along the distal end portion of the delivery shaft assembly, radially between the outer covering shaft and the inner support shaft:
        the delivery shaft assembly is shaped so as to define a self-orienting portion, the self-orienting portion shaped so as to define (a) at least proximal and distal curved portions, wherein the proximal curved portion is disposed more proximal than the distal curved portion, and (b) at least one point of inflection on the central longitudinal axis longitudinally between the proximal and the distal curved portions, and
        respective smallest radii of curvature of the proximal and the distal curved portions, measured at the central longitudinal axis, are each between 2.5 and 12 cm,
    wherein the endovascular system further comprises a distal tip, which is fixed to and extends distally beyond a distal end of the inner support shaft, and
    wherein the self-orienting portion of the delivery shaft assembly is configured to automatically rotationally orient itself to a desired rotational orientation in a blood vessel.

2. The apparatus according to claim 1, wherein the distal end portion of the delivery shaft assembly is shaped so as to define the self-orienting portion.

3. The apparatus according to claim 1, wherein the proximal and the distal curved portions together define a sinusoid.

4. The apparatus according to claim 1, wherein the proximal and the distal curved portions have a same curve shape.

5. The apparatus according to claim 4, wherein the proximal and the distal curved portions are the same size.

6. The apparatus according to claim 1,
    wherein the stent-graft is shaped so as to define a superior lateral opening,
    wherein when the delivery shaft assembly is unconstrained and the stent-graft is removably constrained in the radially-compressed delivery state along the distal end portion of the delivery shaft assembly, radially between outer the covering shaft and the inner support shaft, the stent-graft is axially disposed in the delivery shaft assembly such that the superior lateral opening is in the self-orienting portion, and
    wherein when the delivery shaft assembly is unconstrained and the stent-graft is removably constrained in the radially-compressed delivery state along the distal end portion of the delivery shaft assembly, radially between outer the covering shaft and the inner support shaft, the stent-graft is rotationally oriented with respect to the delivery shaft assembly so as to, upon release of the stent-graft from the delivery shaft assembly without rotation of the stent-graft, define a line between (a) the central longitudinal axis and (b) a central axis of the superior lateral opening parallel to the central longitudinal axis, which line is perpendicular to the central longitudinal axis, and forms an angle of no more than 30 degrees with a proximal best-fit plane defined by the proximal curved portion, wherein the proximal best-fit plane is defined when the delivery shaft assembly is unconstrained and the stent-graft is removably constrained in the radially-compressed delivery state along the distal end portion of the delivery shaft assembly, radially between the outer covering shaft and the inner support shaft.

7. The apparatus according to claim 1, wherein the delivery shaft assembly is shaped so as not to define an additional curved portion, in addition to the proximal and the distal curved portions, having a smallest radius of curvature, measured at the central longitudinal axis, of between 2.5 and 12 cm.

8. The apparatus according to claim 1, wherein the respective smallest radii of curvature of the proximal and the distal curved portions are each between 4 and 10 cm.

9. The apparatus according to claim 1, wherein the distal tip is conical.

10. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
    the self-orienting portion defines a best-fit straight axis line having a minimum sum of squares of distances between the best-fit straight axis line and the central longitudinal axis along the proximal and the distal curved portions,
    the proximal and the distal curved portions have respective proximal and distal peaks with respect to the best-fit straight axis line, which define respective proximal and distal vectors, which (i) have respective origins on the best-fit straight axis line, (ii) are perpendicular to the best-fit straight axis line, and (iii) intersect the proximal and the distal peaks, respectively, and an angle between the proximal and the distal vectors is at least 120 degrees.

11. The apparatus according to claim 10, wherein the angle between the proximal and the distal vectors is at least 150 degrees.

12. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- respective distances between (a) the best-fit straight axis line and (b) the proximal and the distal peaks are each at least 3 cm.

13. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions, and
- the delivery shaft assembly is shaped so as not to define an additional curved portion, in addition to the proximal and the distal curved portions, having a distance between the best-fit straight axis line and a peak of the additional curved portion, with respect to the best-fit straight axis line, of at least 3 cm.

14. The apparatus according to claim 1,
- wherein the self-orienting portion defines a best-fit straight axis line having a minimum sum of squares of distances between the best-fit straight axis line and the central longitudinal axis along the proximal and the distal curved portions, and
- wherein respective axial lengths of the proximal and the distal curved portions, measured parallel to the best-fit straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

15. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- a distance between the proximal and the distal peaks, measured parallel to the best-fit straight axis line, is between 5 and 20 cm.

16. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions have respective proximal and distal peaks with respect to the best-fit straight axis line, and
- a distance between the distal peak and a distal end of the outer covering shaft, measured parallel to the best-fit straight axis line, is between 3 and 8 cm.

17. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the self-orienting portion defines a best-fit straight axis line having a minimum sum of squares of distances between the best-fit straight axis line and the central longitudinal axis along the proximal and the distal curved portions,
- the proximal and the distal curved portions define respective proximal and distal best-fit planes,
- an angle between the proximal and the distal planes is no more than 60 degrees, and
- the proximal and the distal best-fit planes intersect at an intersection line that is not parallel to the best-fit straight axis line.

18. The apparatus according to claim 17, wherein the angle between the proximal and the distal planes is at least 30 degrees.

19. The apparatus according to claim 1, wherein when the delivery shaft assembly is unconstrained and the stent-graft is removably constrained in the radially-compressed delivery state along the distal end portion of the delivery shaft assembly, radially between the outer covering shaft and the inner support shaft:
- the delivery shaft assembly is shaped so as to define a proximal straight portion which is disposed more proximal than the self-orienting portion, and has a length of at least 50 cm,
- the central longitudinal axis along the proximal straight portion defines a straight axis line, and
- the proximal and the distal curved portions have respective proximal and distal peaks with respect to the straight axis line.

20. The apparatus according to claim 19, wherein the proximal and distal peaks define proximal and distal vectors, respectively, which (i) have respective origins on the straight axis line, (ii) are perpendicular to the straight axis line, and (iii) intersect the proximal and the distal peaks, respectively, wherein an angle between the proximal and the distal vectors is at least 120 degrees, when the delivery shaft assembly is unconstrained and the stent-graft is removably constrained in the radially-compressed delivery state along the distal end portion of the delivery shaft assembly, radially between the outer covering shaft and the inner support shaft.

21. The apparatus according to claim 19, wherein respective axial lengths of the proximal and the distal curved portions, measured parallel to the straight axis line, are each between 4 and 18 cm, when the delivery shaft assembly is unconstrained and the stent-graft is removably constrained in the radially-compressed delivery state along the distal end portion of the delivery shaft assembly, radially between the outer covering shaft and the inner support shaft.

22. The apparatus according to claim 19, wherein a distance between the proximal and the distal peaks, measured parallel to the straight axis line, is between 5 and 20 cm, when the delivery shaft assembly is unconstrained and the stent-graft is removably constrained in the radially-compressed delivery state along the distal end portion of the delivery shaft assembly, radially between the outer covering shaft and the inner support shaft.

23. The apparatus according to claim 19, wherein a distance between the distal peak and a distal end of the outer covering shaft, measured parallel to the straight axis line, is between 3 and 8 cm, when the delivery shaft assembly is unconstrained and the stent-graft is removably constrained in the radially-compressed delivery state along the distal end portion of the delivery shaft assembly, radially between the outer covering shaft and the inner support shaft.

\* \* \* \* \*